United States Patent
Gunderson

(10) Patent No.: US 11,717,186 B2
(45) Date of Patent: Aug. 8, 2023

(54) BODY STABILITY MEASUREMENT

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/552,925

(22) Filed: Aug. 27, 2019

(65) Prior Publication Data

US 2021/0059568 A1    Mar. 4, 2021

(51) Int. Cl.
*A61B 5/11*        (2006.01)
*G16H 80/00*   (2018.01)
(Continued)

(52) U.S. Cl.
CPC .......... *A61B 5/1117* (2013.01); *A61B 5/0031* (2013.01); *A61B 5/067* (2013.01); *A61B 5/6801* (2013.01); *G16H 80/00* (2018.01)

(58) Field of Classification Search
CPC ..... A61B 5/1117; A61B 5/0031; A61B 5/067; A61B 5/6801; A61B 5/116; A61B 5/7275; A61B 5/1123; A61B 5/112; A61B 5/0468; A61B 5/686; A61B 5/0456; A61B 2560/0209; A61B 2562/0219; G16H 80/00; G16H 20/30; G16H 50/30; G16H 10/60; G16H 50/20; A61N 1/36542; A61N 1/3962; A61N 1/36564; A61N 1/36592;

(Continued)

(56) References Cited

U.S. PATENT DOCUMENTS 2,009,393 A    7/1935    Gioacchino
4,374,382 A    2/1983    Markowitz
(Continued)

FOREIGN PATENT DOCUMENTS

CN    1031481 A    3/1989
CN    2621634 Y    6/2004
(Continued)

OTHER PUBLICATIONS

"Guideline for the Prevention of Falls in Older Persons—American Geriatrics Society, British Geriatrics Society, and American Academy of Orthopaedic Surgeons Panel on Falls Prevention," Journal of the American Geriatrics Society, vol. 49, No. 5, May 2001, 9 pp.

(Continued)

*Primary Examiner* — Patrick Fernandes
(74) *Attorney, Agent, or Firm* — Shumaker & Sieffert, P.A.

(57) ABSTRACT

A medical device system and method that includes accelerometer circuitry configured to generate at least one signal, a memory, and processing circuitry coupled to the accelerometer circuitry and the memory. The processing circuitry is configured to monitor a patient for a Sit-To-Stand transition based upon the at least one signal, detect the Sit-to-Stand transition, determine if the patient has been inactive for a predetermined period of time prior to the Sit-to-Stand transition, and if the patient has been inactive for at least the predetermined period of time prior to the Sit-to-Stand transition, determine a body stability score of the patient.

20 Claims, 16 Drawing Sheets

(51) Int. Cl.
*A61B 5/00* (2006.01)
*A61B 5/06* (2006.01)

(58) Field of Classification Search
CPC .............. A61N 1/3704; A61N 1/3925; A61N 1/36521; G08B 21/0446; G01P 15/00
See application file for complete search history.

(56) References Cited

U.S. PATENT DOCUMENTS

| | | | |
|---|---|---|---|
| 4,823,797 A | 4/1989 | Heinze et al. |
| 4,915,686 A | 4/1990 | Frederick |
| 5,107,833 A | 4/1992 | Barsness |
| 5,117,824 A | 6/1992 | Keimel et al. |
| 5,127,404 A | 7/1992 | Wyborny et al. |
| 5,168,871 A | 12/1992 | Grevious |
| 5,271,395 A | 12/1993 | Wahlstrand et al. |
| 5,292,343 A | 3/1994 | Blanchette et al. |
| 5,304,119 A | 4/1994 | Balaban et al. |
| 5,314,450 A | 5/1994 | Thompson |
| 5,324,315 A | 6/1994 | Grevious |
| 5,354,319 A | 10/1994 | Wyborny et al. |
| 5,368,040 A | 11/1994 | Carney |
| 5,383,909 A | 1/1995 | Keimel |
| 5,484,403 A | 1/1996 | Yoakum et al. |
| 5,545,186 A | 8/1996 | Olson et al. |
| 5,755,736 A | 5/1998 | Gillberg et al. |
| 5,772,671 A | 6/1998 | Harmon |
| 5,836,975 A | 11/1998 | DeGroot |
| 5,842,999 A | 12/1998 | Pruitt et al. |
| 5,857,975 A | 1/1999 | Golub |
| 5,876,353 A | 3/1999 | Riff |
| 5,913,879 A | 6/1999 | Ferek-Petric et al. |
| 5,954,670 A | 9/1999 | Baker |
| 5,957,861 A | 9/1999 | Combs et al. |
| 5,987,352 A | 11/1999 | Klein et al. |
| 6,024,704 A | 2/2000 | Meador et al. |
| 6,045,513 A | 4/2000 | Stone et al. |
| 6,102,874 A | 8/2000 | Stone et al. |
| 6,104,949 A | 8/2000 | Pitts Crick et al. |
| 6,148,233 A | 11/2000 | Owen et al. |
| 6,154,674 A | 11/2000 | Meier |
| 6,221,011 B1 | 4/2001 | Bardy |
| 6,230,059 B1 | 5/2001 | Duffin |
| 6,263,243 B1 | 7/2001 | Lang |
| 6,277,072 B1 | 8/2001 | Bardy |
| 6,280,380 B1 | 8/2001 | Bardy |
| 6,280,409 B1 | 8/2001 | Stone et al. |
| 6,336,903 B1 | 1/2002 | Bardy |
| 6,405,085 B1 | 6/2002 | Graupner et al. |
| 6,409,675 B1 | 6/2002 | Turcott |
| 6,412,490 B1 | 7/2002 | Lee |
| 6,449,509 B1 | 9/2002 | Park et al. |
| 6,459,929 B1 | 10/2002 | Hopper et al. |
| 6,463,326 B1 | 10/2002 | Hartley et al. |
| 6,466,821 B1 | 10/2002 | Pianca et al. |
| 6,473,640 B1 | 10/2002 | Erlebacher |
| 6,480,733 B1 | 11/2002 | Turcott |
| 6,512,940 B1 | 1/2003 | Brabec et al. |
| 6,512,949 B1 | 1/2003 | Combs et al. |
| 6,522,915 B1 | 2/2003 | Ceballos et al. |
| 6,572,557 B2 | 6/2003 | Tchou et al. |
| 6,595,927 B2 | 7/2003 | Pitts-Crick et al. |
| 6,620,467 B2 | 9/2003 | Sudo et al. |
| 6,622,046 B2 | 9/2003 | Fraley et al. |
| 6,625,493 B2 | 9/2003 | Kroll et al. |
| 6,647,295 B2 | 11/2003 | Florio et al. |
| 6,658,292 B2 | 12/2003 | Kroll et al. |
| 6,671,549 B2 | 12/2003 | Van Dam et al. |
| 6,719,701 B2 | 4/2004 | Lade |
| 6,788,970 B1 | 9/2004 | Park et al. |
| 6,821,249 B2 | 11/2004 | Casscells, III et al. |
| 6,866,629 B2 | 3/2005 | Bardy |
| 6,892,094 B2 | 5/2005 | Ousdigian et al. |
| 6,895,275 B2 | 5/2005 | Markowitz et al. |
| 6,907,288 B2 | 6/2005 | Daum |
| 6,931,272 B2 | 8/2005 | Burnes |
| 6,945,934 B2 | 9/2005 | Bardy |
| 6,960,167 B2 | 11/2005 | Bardy |
| 7,029,447 B2 | 4/2006 | Rantala |
| 7,035,684 B2 | 4/2006 | Lee |
| 7,127,290 B2 | 10/2006 | Girouard et al. |
| 7,141,026 B2 | 11/2006 | Aminian et al. |
| 7,149,584 B1 | 12/2006 | Koh et al. |
| 7,177,681 B2 | 2/2007 | Zhu |
| 7,177,684 B1 | 2/2007 | Kroll et al. |
| 7,184,821 B2 | 2/2007 | Belalcazar et al. |
| 7,248,916 B2 | 7/2007 | Bardy |
| 7,272,442 B2 | 9/2007 | Freeberg |
| 7,308,309 B1 | 12/2007 | Koh |
| 7,310,551 B1 | 12/2007 | Koh et al. |
| 7,313,434 B2 | 12/2007 | Belalcazar et al. |
| 7,340,296 B2 | 3/2008 | Stahmann et al. |
| 7,387,610 B2 | 6/2008 | Stahmann et al. |
| 7,389,143 B2 | 6/2008 | Hopper et al. |
| 7,541,934 B2 | 6/2009 | Fredriksson et al. |
| 7,636,602 B2 | 12/2009 | Baru Fassio et al. |
| 7,647,106 B2 | 1/2010 | Virag et al. |
| 7,848,810 B1 | 12/2010 | Nabutovsky et al. |
| 7,937,135 B2 | 5/2011 | Ghanem et al. |
| 7,991,471 B2 | 8/2011 | Ghanem et al. |
| 7,996,087 B2 | 8/2011 | Cowan et al. |
| 8,027,726 B2 | 9/2011 | Ternes |
| 8,206,325 B1 | 6/2012 | Najaf et al. |
| 8,255,046 B2 | 8/2012 | Sarkar et al. |
| 8,428,720 B2 | 4/2013 | Corbucci et al. |
| 8,475,370 B2 | 7/2013 | McCombie et al. |
| 8,491,504 B2 | 7/2013 | Hirth |
| 8,521,281 B2 | 8/2013 | Patel et al. |
| 8,736,453 B2 | 1/2014 | Wilson et al. |
| 8,688,201 B2 | 4/2014 | Corbucci et al. |
| 8,744,572 B1 | 6/2014 | Greenhut et al. |
| 8,818,505 B2 | 8/2014 | Bhunia et al. |
| 8,845,557 B1 | 9/2014 | Giuffrida et al. |
| 8,886,296 B2 | 11/2014 | Patel |
| 8,888,745 B2 | 11/2014 | Van Der Graaf et al. |
| 8,990,041 B2 | 3/2015 | Grabiner et al. |
| 9,005,141 B1 | 4/2015 | Najaf et al. |
| 9,318,012 B2 | 4/2016 | Johnson et al. |
| 9,332,924 B2 | 5/2016 | Thakur et al. |
| 9,403,000 B2 | 8/2016 | Lyons et al. |
| 9,452,101 B2 | 9/2016 | Tomlinson et al. |
| 9,526,522 B2 | 12/2016 | Wood et al. |
| 9,675,279 B2 | 6/2017 | Henning |
| 9,795,322 B1 * | 10/2017 | Karunaratne ............ A47C 7/62 |
| 9,826,939 B2 | 11/2017 | Averina et al. |
| 9,848,778 B2 | 12/2017 | Soykan et al. |
| 9,901,290 B2 | 2/2018 | Najaf et al. |
| 9,907,959 B2 | 3/2018 | Skelton |
| 10,032,069 B2 | 7/2018 | Mizuochi et al. |
| 10,052,062 B2 | 8/2018 | De Sapio et al. |
| 10,070,824 B2 | 9/2018 | LeLorier |
| 10,124,172 B2 | 11/2018 | Lyons et al. |
| 10,166,001 B2 | 1/2019 | An et al. |
| 10,182,729 B2 | 1/2019 | Zielinski et al. |
| 10,252,068 B2 | 4/2019 | Gunderson et al. |
| 10,264,997 B1 | 4/2019 | Romrell et al. |
| 10,335,047 B2 | 7/2019 | Gunderson |
| 10,506,933 B2 | 12/2019 | Soykan et al. |
| 10,610,132 B2 | 4/2020 | Gunderson et al. |
| 10,765,359 B2 | 9/2020 | Cho et al. |
| 10,850,113 B2 | 12/2020 | Cao et al. |
| 10,952,686 B2 | 3/2021 | Gunderson et al. |
| 2001/0004234 A1 | 6/2001 | Petelenz et al. |
| 2001/0011153 A1 | 8/2001 | Bardy |
| 2001/0021801 A1 | 9/2001 | Bardy |
| 2001/0039504 A1 | 11/2001 | Lindberg et al. |
| 2002/0004672 A1 | 1/2002 | Florio et al. |
| 2002/0026103 A1 | 2/2002 | Norris et al. |
| 2002/0026104 A1 | 2/2002 | Bardy |
| 2002/0058969 A1 | 5/2002 | Noren et al. |
| 2002/0115939 A1 | 8/2002 | Mulligan et al. |
| 2002/0132044 A1 | 9/2002 | Quarles |
| 2003/0028221 A1 | 2/2003 | Zhu et al. |
| 2003/0055461 A1 | 3/2003 | Girouard et al. |

(56) References Cited

U.S. PATENT DOCUMENTS

| | | |
|---|---|---|
| 2003/0125611 A1 | 7/2003 | Bardy |
| 2003/0149367 A1 | 8/2003 | Kroll et al. |
| 2003/0212445 A1 | 11/2003 | Weinberg |
| 2003/0220580 A1 | 11/2003 | Alt |
| 2004/0015197 A1 | 1/2004 | Gunderson |
| 2004/0082969 A1 | 4/2004 | Kerr |
| 2004/0102712 A1 | 5/2004 | Belalcazar et al. |
| 2004/0112151 A1 | 6/2004 | Maxwell et al. |
| 2004/0122484 A1 | 6/2004 | Hatlestad et al. |
| 2004/0172080 A1 | 9/2004 | Stadler et al. |
| 2004/0193154 A1 | 9/2004 | Leatherbury et al. |
| 2004/0220633 A1 | 11/2004 | Wagner et al. |
| 2004/0249388 A1 | 12/2004 | Michelson |
| 2005/0090852 A1 | 4/2005 | Layne et al. |
| 2005/0096645 A1 | 5/2005 | Wellman et al. |
| 2005/0107768 A1 | 5/2005 | Ting |
| 2005/0115561 A1 | 6/2005 | Stahmann et al. |
| 2005/0124908 A1 | 6/2005 | Belalcazar et al. |
| 2005/0137626 A1 | 6/2005 | Pastore et al. |
| 2006/0020295 A1 | 1/2006 | Brockway et al. |
| 2006/0030892 A1 | 2/2006 | Kadhiresan et al. |
| 2006/0041281 A1 | 2/2006 | Von Arx et al. |
| 2006/0074434 A1 | 4/2006 | Wenstrom et al. |
| 2006/0095085 A1 | 5/2006 | Marcus et al. |
| 2006/0097331 A1 | 5/2006 | Hattori et al. |
| 2006/0106415 A1 | 5/2006 | Gabbay |
| 2006/0174898 A1 | 8/2006 | Brown |
| 2006/0241701 A1 | 10/2006 | Markowitz et al. |
| 2006/0276848 A1 | 12/2006 | Min et al. |
| 2006/0293609 A1 | 12/2006 | Stahmann et al. |
| 2007/0010738 A1 | 1/2007 | Mark et al. |
| 2007/0021678 A1 | 1/2007 | Beck et al. |
| 2007/0032749 A1 | 2/2007 | Overall et al. |
| 2007/0067005 A1 | 3/2007 | Schatz et al. |
| 2007/0088394 A1 | 4/2007 | Jacobson |
| 2007/0088397 A1 | 4/2007 | Jacobson |
| 2007/0129765 A1 | 6/2007 | Gilkerson et al. |
| 2007/0142732 A1 | 6/2007 | Brockway et al. |
| 2007/0156061 A1 | 7/2007 | Hess |
| 2007/0179515 A1 | 8/2007 | Matsutani et al. |
| 2007/0249992 A1 | 10/2007 | Bardy |
| 2008/0024293 A1 | 1/2008 | Stylos |
| 2008/0027349 A1 | 1/2008 | Stylos |
| 2008/0082001 A1 | 4/2008 | Hatlestad et al. |
| 2008/0154298 A1 | 6/2008 | Grayzel et al. |
| 2008/0161657 A1 | 7/2008 | Bullens et al. |
| 2008/0183083 A1 | 7/2008 | Markowitz et al. |
| 2008/0255626 A1 | 10/2008 | Fricke et al. |
| 2008/0281550 A1 | 11/2008 | Hogle et al. |
| 2008/0288200 A1 | 11/2008 | Noble |
| 2009/0030426 A1 | 1/2009 | Zinn et al. |
| 2009/0036917 A1 | 2/2009 | Anderson |
| 2009/0137946 A1 | 5/2009 | Nassiri et al. |
| 2009/0171228 A1 | 7/2009 | Fischell et al. |
| 2009/0221937 A1 | 9/2009 | Smith et al. |
| 2009/0278934 A1 | 11/2009 | Ecker et al. |
| 2009/0281399 A1 | 11/2009 | Keel et al. |
| 2009/0312649 A1 | 12/2009 | Lian et al. |
| 2010/0010361 A1 | 1/2010 | Boute et al. |
| 2010/0030090 A1 | 2/2010 | Zhang et al. |
| 2010/0030227 A1 | 2/2010 | Kast et al. |
| 2010/0030292 A1 | 2/2010 | Sarkar et al. |
| 2010/0030293 A1 | 2/2010 | Sarkar et al. |
| 2010/0057157 A1 | 3/2010 | Govari et al. |
| 2010/0087745 A1 | 4/2010 | Fischell et al. |
| 2010/0094252 A1 | 4/2010 | Wengreen et al. |
| 2010/0011424 A1 | 5/2010 | Donofrio et al. |
| 2010/0114241 A1 | 5/2010 | Donofrio et al. |
| 2010/0198097 A1 | 8/2010 | Sowelam |
| 2010/0198140 A1 | 8/2010 | Lawson |
| 2010/0210975 A1 | 8/2010 | Anthony, III et al. |
| 2010/0228308 A1 | 9/2010 | Cowan et al. |
| 2010/0331868 A1 | 12/2010 | Bardy |
| 2011/0040572 A1 | 2/2011 | Chmiel et al. |
| 2011/0071586 A1 | 3/2011 | Jacobson |
| 2011/0077865 A1 | 3/2011 | Chen et al. |
| 2011/0082350 A1 | 4/2011 | Koh |
| 2011/0106201 A1 | 5/2011 | Bhunia |
| 2011/0148400 A1 | 6/2011 | Doerr et al. |
| 2011/0172545 A1 | 7/2011 | Grudic et al. |
| 2011/0172562 A1 | 7/2011 | Sahasrabudhe et al. |
| 2011/0190835 A1 | 8/2011 | Brockway et al. |
| 2011/0224498 A1 | 9/2011 | Banet et al. |
| 2012/0083705 A1 | 4/2012 | Yuen et al. |
| 2012/0109235 A1 | 5/2012 | Jacobson |
| 2012/0109236 A1 | 5/2012 | Jacobson et al. |
| 2012/0109237 A1 | 5/2012 | Xiao et al. |
| 2012/0157874 A1 | 6/2012 | Thakur et al. |
| 2012/0259577 A1* | 10/2012 | Ganyi ............... G08B 21/0446 702/139 |
| 2012/0271177 A1 | 10/2012 | Emerson et al. |
| 2012/0277546 A1 | 11/2012 | Soykan et al. |
| 2012/0283705 A1 | 11/2012 | Lee et al. |
| 2013/0079861 A1 | 3/2013 | Reinert et al. |
| 2013/0085677 A1 | 4/2013 | Modi et al. |
| 2013/0096449 A1 | 4/2013 | Patel et al. |
| 2013/0123617 A1 | 5/2013 | Caros et al. |
| 2013/0123684 A1 | 5/2013 | Giuffida et al. |
| 2013/0066169 A1 | 9/2013 | Rys et al. |
| 2013/0304414 A1 | 11/2013 | Levy et al. |
| 2014/0022079 A1 | 1/2014 | Wilson et al. |
| 2014/0024871 A1 | 1/2014 | Kanagawa et al. |
| 2014/0024971 A1 | 1/2014 | Bunn et al. |
| 2014/0088442 A1 | 3/2014 | Soykan et al. |
| 2014/0128778 A1 | 5/2014 | Chan et al. |
| 2014/0128963 A1 | 5/2014 | Quill et al. |
| 2014/0275916 A1 | 9/2014 | Nabutovsky et al. |
| 2014/0276130 A1 | 9/2014 | Mirelman et al. |
| 2014/0276928 A1 | 9/2014 | Venderpool et al. |
| 2014/0330172 A1 | 11/2014 | Jovanov |
| 2014/0358193 A1 | 12/2014 | Lyons et al. |
| 2014/0364769 A1 | 12/2014 | Chang et al. |
| 2015/0011840 A1 | 1/2015 | Gavriely |
| 2015/0164437 A1 | 6/2015 | Mccombie et al. |
| 2015/0185044 A1 | 7/2015 | Nie et al. |
| 2015/0257654 A1 | 9/2015 | Bennett-Guerrero |
| 2015/0283383 A1 | 10/2015 | Ternes et al. |
| 2015/0286285 A1 | 10/2015 | Pantelopoulos et al. |
| 2015/0302720 A1* | 10/2015 | Zhang ............... G08B 21/0446 340/573.7 |
| 2015/0313552 A1 | 11/2015 | Zhang et al. |
| 2015/0342540 A1 | 12/2015 | An et al. |
| 2016/0038093 A1 | 2/2016 | Sharma et al. |
| 2016/0045140 A1 | 2/2016 | Kitamura et al. |
| 2016/0058333 A1* | 3/2016 | Arnold ............... A63B 22/0605 702/19 |
| 2016/0100776 A1 | 4/2016 | Najaf et al. |
| 2016/0155313 A1 | 6/2016 | Chang et al. |
| 2016/0175007 A1 | 6/2016 | Valbuena et al. |
| 2016/0192890 A1 | 7/2016 | Averina et al. |
| 2016/0209232 A1 | 7/2016 | Yang et al. |
| 2016/0220153 A1 | 8/2016 | Annegarn et al. |
| 2016/0310031 A1 | 10/2016 | Sarkar |
| 2017/0056666 A1 | 3/2017 | Kane et al. |
| 2017/0067933 A1 | 3/2017 | Miller et al. |
| 2017/0112463 A1 | 4/2017 | An et al. |
| 2017/0119263 A1 | 5/2017 | Hill |
| 2017/0155877 A1 | 6/2017 | Johnson et al. |
| 2017/0188897 A1 | 7/2017 | Thein et al. |
| 2017/0213145 A1 | 7/2017 | Pathak et al. |
| 2017/0258346 A1 | 9/2017 | Vanderpool et al. |
| 2017/0332952 A1 | 11/2017 | Desborough et al. |
| 2017/0344919 A1 | 11/2017 | Chang et al. |
| 2018/0035898 A1 | 2/2018 | Gunderson |
| 2018/0035920 A1 | 2/2018 | Gunderson et al. |
| 2018/0035924 A1 | 2/2018 | Gunderson et al. |
| 2018/0035956 A1* | 2/2018 | Gunderson ............ A61B 5/686 |
| 2018/0055386 A1 | 3/2018 | Zielinski et al. |
| 2018/0070889 A1 | 3/2018 | Lee et al. |
| 2018/0103874 A1 | 4/2018 | Lee et al. |
| 2018/0168461 A1 | 6/2018 | Morris et al. |
| 2018/0168502 A1 | 6/2018 | Cho et al. |
| 2018/0177436 A1 | 6/2018 | Chang et al. |
| 2018/0333083 A1 | 11/2018 | Orellano |

(56) References Cited

U.S. PATENT DOCUMENTS

| | | |
|---|---|---|
| 2019/0069851 A1 | 3/2019 | Sharma et al. |
| 2019/0103007 A1 | 4/2019 | Tan et al. |
| 2019/0150852 A1 | 5/2019 | Stone et al. |
| 2019/0167205 A1 | 6/2019 | An et al. |
| 2019/0214146 A1 | 7/2019 | Dunias et al. |
| 2020/0174517 A1 | 6/2020 | Martinez et al. |
| 2020/0187864 A1 | 6/2020 | Sharma |
| 2020/0187866 A1 | 6/2020 | Antunes et al. |
| 2020/0297230 A1 | 9/2020 | Thakur et al. |
| 2020/0323452 A1 | 10/2020 | Mahajan et al. |
| 2020/0352521 A1 | 11/2020 | Chakravarthy et al. |
| 2021/0093253 A1 | 4/2021 | Sarkar et al. |
| 2022/0273236 A1 | 5/2022 | Zhou |

FOREIGN PATENT DOCUMENTS

| | | |
|---|---|---|
| CN | 2702718 Y | 6/2005 |
| CN | 1767872 A | 5/2006 |
| CN | 101676004 A | 3/2010 |
| CN | 102027379 A | 4/2011 |
| CN | 202342097 U | 7/2012 |
| CN | 104799933 A | 7/2015 |
| CN | 104812439 A | 7/2015 |
| CN | 104939819 A | 9/2015 |
| CN | 105101869 A | 11/2015 |
| CN | 105311814 A | 2/2016 |
| DE | 469951 C | 1/1929 |
| DE | 4243641 A1 | 9/1994 |
| DE | 10148440 A1 | 4/2003 |
| EP | 1997427 A1 | 3/2008 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 9833554 A1 | 8/1998 |
| WO | 200064336 A1 | 11/2000 |
| WO | 2001032260 A1 | 5/2001 |
| WO | 2002067449 A2 | 8/2002 |
| WO | 2003061759 A1 | 7/2003 |
| WO | 2004093985 A1 | 11/2004 |
| WO | 2005044116 A2 | 5/2005 |
| WO | 2005060306 A1 | 6/2005 |
| WO | 2006/070124 A1 | 7/2006 |
| WO | 2006081432 A1 | 8/2006 |
| WO | 2007033194 A2 | 3/2007 |
| WO | 2007/079354 A2 | 7/2007 |
| WO | 2008016551 A1 | 2/2008 |
| WO | 2010030942 A1 | 3/2010 |
| WO | 2012/098356 A1 | 7/2012 |
| WO | 2012098356 A1 | 7/2012 |
| WO | 2014083538 A1 | 6/2014 |
| WO | 2017142488 A1 | 8/2017 |
| WO | 2020002566 A1 | 1/2020 |

OTHER PUBLICATIONS

Clark et al., "Improving the Validity of Activity of Daily Living Dependency Risk Assessment," Journal of Applied Gerontology: The Official Journal of the Southern Gerontological Society, vol. 34, No. 3, Apr. 2015, 14 pp.

Devries et al., "Outcome instruments to measure frailty: A systematic review," Ageing Research Reviews, vol. 10, accepted Sep. 2010, published Jan. 2011, 11 pp.

Kearns et al., "Path Tortuosity in Everyday Movements of Elderly Persons Increases Fall Prediction Beyond Knowledge of Fall History, Medication Use and Standardized Gait and Balance Assessments," Journal of the American Medical Directors Association, (JAMDA), vol. 13, No. 7, Sep. 2012, 7 pp.

Kearns et al., "Tortuosity in Movement Paths Is Related to Cognitive Impairment—Wireless Fractal Estimation in Assisted Living Facility Residents," Methods of Information in Medicine, vol. 49, No. 6, Mar. 2010, 7 pp.

Kearns et al., "Wireless telesurveillance system for detecting dementia," Gerontechnology, vol. 10, No. 2, Jan. 2011, 13 pp.

Mccrory et al., "Speed of Heart Rate Recovery in Response to Orthostatic Challenge—A Strong Risk Marker of Mortality," Circulation Research, vol. 119, No. 5, Aug. 2016, 10 pp.

Millor et al., "Kinematic Parameters to Evaluate Functional Performance of Sit-to-Stand and Stand-to-Sit Transitions Using Motion Sensor Devices: a Systematic Review," IEEE Transactions on Neural Systems and Rehabilitation Engineering, vol. 22, No. 5, Jun. 2014, 11 pp.

Odden et al., "Rethinking the Association of High Blood Pressure With Mortality in Elderly Adults: The Impact of Frailty," Archives of Internal Medicine, vol. 172, No. 15, Aug. 2012, 7 pp.

Robertson et al., "Frailty and Cognitive impairment—A review of the evidence and causal mechanisms," Ageing Research Reviews, vol. 12, No. 4, Sep. 2013, 12 pp.

Romero-Ortuno et al., "A Frailty Instrument for primary care: findings from the Survey of Health, Ageing and Retirement in Europe (SHARE)," BMC Geriatrics, vol. 10, No. 57, Aug. 2010, 12 pp.

U.S. Appl. No. 16/940,817, filed Jul. 28, 2020, by Burnes et al.

International Search Report and Written Opinion of International Application No. PCT/US2020/039489, dated Oct. 8, 2020, 9 pp.

Ganea et al., "Multi-Parametric Evaluation of Sit-to-Stand and Stand-to-Sit Transitions in Elderly People," Medical Engineering and Physics, vol. 33. No. 9, Apr. 23, 2011, pp. 1086-1093.

Final Office Action from U.S. Appl. No. 15/604,044, dated Nov. 12, 2020, 30 pp.

Response filed on Nov. 2, 2020 to Final Office Action dated Sep. 2, 2020 from U.S. Appl. No. 15/607,945, 8 pp.

Adamson et al, "Continuous Autonomic Assessment in Patients with Symptomatic Heart Failure . . . " Circulation Journal of American Heart Association, pp. 2389-2394. 110: 16, Jun. 30, 2004.

Alberts et al., "Using Accelerometer and Gyroscopic Measures to Quantify Postural Stability," Journal of Athletic Training, vol. 50, No. 6, Jun. 2015, 11 pp.

Baer, et al. "Electronic Home Monitoring of Congestive Heart Failure Patients: Design and Feasibility", Congestive Heart Failure, 5:105-113, May/Jun. 1999.

Barde, "What to use to express the variability of data: Standard deviation or standard error of mean?," Perspectives In clinical Research, Jul. 2012, 4 pp.

Berman et al. "Transthoracic Electrical Impedance as a Guide to Intravascular Overload", Archives Surgery, 102, pp. 61-62, Jan. 1971.

Chang et al., "A Wireless Accelerometer-Based Body Posture Stability Detection System and Its Application for Meditation Practitioners," Sensors, ISSN: 1424-8220, Dec. 18, 2012, 13 pp.

Giuberti et al., "Automatic UPDRS Evaluation in the Sit-to-Stand Task of Parkinsonians: Kinetic Analysis and Comparative Outlook on the Leg Agility Task", IEEE Journal of Biomedical and Health Informatics, May 2015, pp. 168-2194, vol. 19, No. 3.

Hubble et al., "Wearable Sensor Use for Assessing Standing Balance and Walking Stability in People with Parkinson's Disease: A Systematic Review," PLOS One, Apr. 20, 2015, 22 pp.

Lusignan, et al. "Compliance and Effectiveness of 1 Year's Home Telemonitoring,The Report of a Pilot Study . . . " European Journal of Heart Failure, 3:723-730, Apr. 2001.

Rigoberto et al., "Postural sway parameters using a triaxial accelerometer: Comparing elderly and young healthy adults," Computer Methods in Biomechanics and Biomedical Engineering, Feb. 21, 2011, 12 pp.

Veltink, et al., "Detection of Static and Dynamic Activities Using Uniaxial Accelerometers", IEEE Transacations on Rehabilitation Engineering, Dec. 1996, 11 pp., vol. 4, No. 4.

Wieling et al., "Testing for Autonomic Neuropathy: Heart Rate Changes After Orthostatic Manoeuvers and Static Muscle Contractions," Clinical Science(London), Jun. 1, 1983, pp. 581-586, vol. 64, No. 6.

(56) References Cited

OTHER PUBLICATIONS

Wuerz et al., "Effects of Prehospital Medications on Mortality and Length of Stay in Congestive Heart Failure", Annals of Emergency Medicine 21:6 pp. 669-674. Jun. 1992.
Prosecution History from U.S. Appl. No. 13/614,004, dated Jun. 20, 2013 through Apr. 24, 2014, 75 pp.
Prosecution History from U.S. Appl. No. 15/605,100, dated Aug. 7, 2019 through Dec. 23, 2019, 75 pp.
Prosecution History from U.S. Appl. No. 15/603,776, dated Sep. 18, 2019 through Jan. 10, 2020, 16 pp.
Prosecution History from U.S. Appl. No. 15/603,901, dated Jun. 13, 2018 through Feb. 25, 2019, 87 pp.
Prosecution History from U.S. Appl. No. 15/604,044, dated Jun. 14, 2019 through Jan. 8, 2020, 93 pp.
Prosecution History from U.S. Appl. No. 15/607,945, dated Jan. 17, 2019 through Oct. 3, 2019, 30 pp.
Office Action from U.S. Appl. No. 15/604,044, dated Jun. 1, 2020, 26 pp.
Amendment in Response to Office Action dated Mar. 6, 2020, from U.S. Appl. No. 15/607,945, filed Jul. 1, 2020, 15 pp.
Pre-Appeal Brief Request for Review for U.S. Appl. No. 15/605,100, filed Mar. 26, 2021, 5 pp.
Notice of Appeal for U.S. Appl. No. 15/605,100, filed Mar. 26, 2021, 1 pp.
Appeal Brief for U.S. Appl. No. 15/604,044, filed Mar. 23, 2021, 35 pp.
U.S. Appl. No. 17/181,199, by Inventors: Gunderson et al., filed Feb. 22, 2021.
Office Action from U.S. Appl. No. 15/607,945, dated Mar. 6, 2020, 14 pp.
Advisory Action from U.S. Appl. No. 15/605,100, dated Feb. 28, 2020, 3 pp.
Advisory Action from U.S. Appl. No. 15/605,100, dated Feb. 23, 2021, 4 pp.
Amendment under 37 CFR 41.33 from U.S. Appl. No. 15/604,044, filed Mar. 15, 2021, 9 pp.
Pre-Appeal Brief Decision from U.S. Appl. No. 15/605,100, dated May 5, 2021, 2 pp.
Advisory Action from U.S. Appl. No. 15/604,044, dated Mar. 26, 2021, 3 pp.
Examiner's Answer from U.S. Appl. No. 15/604,044, dated May 13, 2021, 18 pp.
Prosecution History from U.S. Appl. No. 15/607,945, dated Jan. 17, 2019 through Dec. 23, 2020, 119 pp.
Final Office Action from U.S. Appl. No. 15/605,100, dated Dec. 28, 2020, 35 pp.
Response to Final Office Action dated Dec. 28, 2020, from U.S. Appl. No. 15/605,100, filed Feb. 3, 2021, 8 pp.
Notice of Appeal for U.S. Appl. No. 15/604,044, filed Feb. 4, 2021, 1 pp.
Final Office Action from U.S. Appl. No. 15/607,945, dated Sep. 2, 2020, 18 pp.
Ganea et al., "Kinematics and dynamic complexity of postural transitions in frail elderly subjects," Proceedings of the 29th Annual International Conference of the IEEE EMBS, Aug. 23-26, 2007, 4 pp.
Response to Office Action dated Jul. 6, 2020, from U.S. Appl. No. 15/605,100, filed Sep. 21, 2020, 17 pp.
Response to Office Action dated Jun. 1, 2020, from U.S. Appl. No. 15/604,044, filed Aug. 11, 2020, 24 pp.
Office Action from U.S. Appl. No. 15/605,100, dated Jul. 6, 2020, 34 pp.
Amendment in Response to Office Action dated Dec. 23, 2019, from U.S. Appl. No. 15/605,100, filed Feb. 5, 2020, 13 pp.
Amendment in Response to Office Action dated Nov. 13, 2019, from U.S. Appl. No. 15/604,044, filed Feb. 11, 2020, 25 pp.
Advisory Action from U.S. Appl. No. 15/604,044, dated Jan. 30, 2020, 3 pp.
Notice of Allowance from U.S. Appl. No. 15/603,776, dated Jan. 10, 2020, 7 pp.
Notice of Allowance from U.S. Appl. No. 15/607,945, dated Dec. 23, 2020, 7 pp.
Reply Brief from co-pending U.S. Appl. No. 15/604,044, filed Jul. 6, 2021, 14 pp.
Monnet et al., "Comparison of Algorithms to Determine Jump Height and Flight Time from Body Mounted Accelerometers," Sports Engineering, vol. 17 No. 4, Jun. 17, 2014, 21 pages.
Goutterbarge et al., "Reproducibility and Validity of the Myotest for Measuring Step Frequency and Ground Contact Time in Recreational Runners," Journal of Human Kinetics, vol. 45 No. 1, Mar. 2015, pp. 19-26.
Office Action from U.S. Appl. No. 15/605,100, dated Aug. 18, 2021, 19 pp.
International Search Report and Written Opinion of International Application No. PCT/US2020/039489, dated Aug. 10, 2020, 9 pp.
Office Action from U.S. Appl. No. 15/605,100, dated Nov. 10, 2021, 21 pp.
Advisory Action from U.S. Appl. No. 15/605,100, dated Jun. 3, 2022, 8 pp.
Auricchio et al., "Reducing Ventricular Pacing Frequency in Patients with Atrioventricular Block", Advances in Arrhythmia and Electrophysiology, vol. 9, No. 9, American Heart Association, Sep. 16, 2016, p. 10.
Bereski-Reguig et al., "A New System for Measurement of the Pulse Transit Time, the Pulse Wave Velocity and its Analysis", World Scientific, Journal of Mechanics in Medicine and Biology, vol. 17, No. 1, Apr. 2016, 21 pp.
Decision on Appeal from U.S. Appl. No. 15/604,044, dated Jul. 5, 2022, 28 pp.
Final Office Action from U.S. Appl. No. 15/605,100, dated Feb. 8, 2022, 27 pp.
Response to Final Office Action dated Feb. 8, 2022, and Advisory Action filed Jun. 3, 2022, from U.S. Appl. No. 15/605,100, filed Jun. 8, 2022, 10 pp.
Response to Final Office Action dated Feb. 8, 2022, from U.S. Appl. No. 15/605,100, filed May 2, 2022, 20 pp.
Response to Office Action dated Aug. 18, 2021, from U.S. Appl. No. 15/605,100, filed Nov. 10, 2021, 21 pp.
U.S. Appl. No. 17/804,259, filed May 26, 2022 naming inventors Ya-Jian Cheng et al.
Office Action from U.S. Appl. No. 15/605,100 dated Jul. 12, 2022, 24 pp.
Appeal Brief from U.S. Appl. No. 15/605,100, filed Jan. 11, 2023, 35 pp.
Examiner's Answer from U.S. Appl. No. 15/605,100 dated Mar. 3, 2023, 20 pp.
Reply Brief from U.S. Appl. No. 15/605,100, filed May 2, 2023, 20 pp.

* cited by examiner

BODY STABILITY MEASUREMENT

TECHNICAL FIELD

The disclosure relates generally to device systems, and more particularly to device systems configured to predict the likelihood that a person, such as a patient, may fall based on accelerometer-generated data.

BACKGROUND

Implantable medical devices (IMDs) and external, e.g., wearable, medical devices, including implantable pacemakers and implantable cardioverter-defibrillators (ICDs) and insertable cardiac monitors without therapies (e.g. Medtronic LINQ™), record cardiac electrogram (EGM) signals for sensing cardiac events, e.g., P-waves and R-waves. IMDs detect episodes of bradycardia, tachycardia and/or fibrillation from the sensed cardiac events, and some IMDs respond to the episodes as needed with pacing therapy or high-voltage anti-tachyarrhythmia shocks, e.g., cardioversion or defibrillation shocks. These and other medical devices may include, or be part of a system that includes, sensors that generate other physiological-based signals, such as signals that vary based on patient movement or activity, cardiovascular pressure, blood oxygen saturation, edema, or thoracic impedance.

SUMMARY

In general, this disclosure is directed to techniques for determining an increase in the likelihood a patient may fall based on accelerometer-generated data. More particularly, this disclosure contemplates a medical device that monitors the patient for a sit to stand transition and determines a body stability parameter or score of the patient based on accelerometer-generated data around the sit to stand transition.

In other examples, a device is disclosed comprising: accelerometer circuitry configured to generate at least one signal; a memory; and processing circuitry coupled to the accelerometer circuitry and the memory configured to: detect a Sit-to-Stand transition of a patient based upon the at least one signal; determine if the patient has been inactive for a predetermined period of time prior to the Sit-to-Stand transition; and if the patient has been inactive for at least the predetermined period of time prior to the Sit-to-Stand transition, determine a body stability score of the patient based on the at least one signal.

In other examples, a method is disclosed comprising: detecting a Sit-to-Stand transition of a patient based on at least one accelerometer signal; determining if the patient has been inactive for a predetermined period of time prior to the Sit-to-Stand transition; and if the patient has been inactive for at least the predetermined period of time prior to the Sit-to-Stand, determining a body stability score of the patient based on the at least one accelerometer signal.

In other examples, a non-transitory computer-readable storage medium is disclosed comprising instructions, that when executed by processing circuitry of a device, cause the device to: detect a Sit-to-Stand transition of a patient based upon at least one accelerometer signal; determine if the patient has been inactive for a predetermined period of time prior to the Sit-to-Stand transition; and if the patient has been inactive for at least the predetermined period of time prior to the Sit-to-Stand transition, determine a body stability score of the patient based upon the at least one accelerometer signal.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Implantable medical devices (IMDs) and external, e.g., wearable, medical devices, including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events, and some IMDs respond to the episodes as needed with pacing therapy or high-voltage anti-tachyarrhythmia shocks, e.g., cardioversion or defibrillation shocks. These and other medical devices may include, or be part of a system that includes, sensors that generate other physiological-based signals, such as signals that vary based on patient movement or activity, cardiovascular pressure, blood oxygen saturation, edema, or thoracic impedance. According to the features or aspects of this disclosure, one or more of such signals may be leveraged to provide an objective measure of a patient's body stability.

For example, a medical device system according to certain features or aspects of this disclosure includes accelerometer circuitry configured to generate a number of signals including a sagittal (frontal) axis signal, as well as processing circuitry configured to calculate a patient-specific body stability score based on accelerometer-generated data surrounding Sit-To-Stand transition from the sagittal axis signal, transverse axis signal and/or the vertical axis. Such an implementation may, among other things, provide an objective measure of change (or not) in well-being to help guide therapies, because a patient-specific body stability score based on accelerometer-generated data surrounding a Sit-To-Stand transition can help determine whether health is improving, declining, or stable. Although not so limited, an appreciation of the various aspects of the present disclosure may be gained from the following discussion in connection with the drawings. While this disclosure may provide examples, including identifying medical devices that may be configured to implement the techniques described herein, these identifications are not meant to be limiting. Any device having an accelerometer may be used to implement the techniques of this disclosure.

Figure 1:
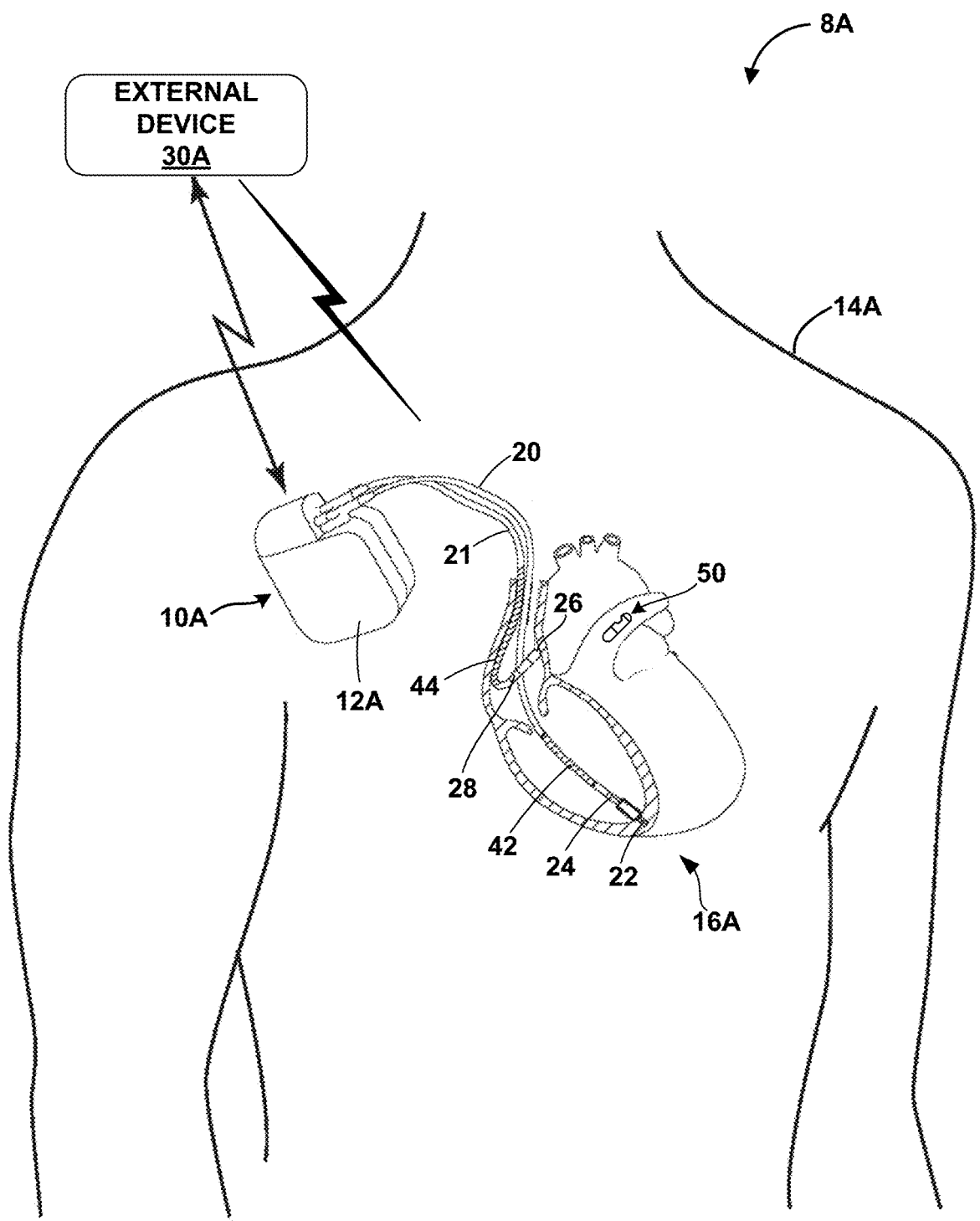
FIG. 1 is a conceptual drawing illustrating an example medical device system in conjunction with a patient.

For example, FIG. 1 is a conceptual drawing illustrating an example medical device system 8A in conjunction with a patient 14A. Medical device system 8A is an example of a medical device system configured to implement the techniques described herein for determining a patient's body stability based on accelerometer-generated data. In the illustrated example, medical device system 8A includes an implantable medical device (IMD) 10A coupled to a ventricular lead 20 and an atrial lead 21. IMD 10A is an implantable cardioverter-defibrillator (ICD) capable of delivering pacing, cardioversion and defibrillation therapy to the heart 16A of a patient 14A, and will be referred to as ICD 10A hereafter.

Ventricular lead 20 and atrial lead 21 are electrically coupled to ICD 10A and extend into the patient's heart 16A. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 1.

ICD 10A may use both ventricular lead 20 and atrial lead 21 to acquire cardiac electrogram (EGM) signals from patient 14A and to deliver therapy in response to the acquired data. Medical device system 8A is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10A may transmit EGM signal data and cardiac rhythm episode data acquired by ICD 10A, as well as data regarding delivery of therapy by ICD 10A, as well as data in manipulated and/or in raw form, possibly compressed, encoded, and/or the like, associated with a patient's body stability as derived from accelerometer-generated data, to an external device 30A. External device 30A may be a computing device, e.g., used in a home, ambulatory, clinic, or hospital setting, to communicate with ICD 10A via wireless telemetry. External device 30A may be coupled to a remote monitoring system, such as Carelink®, available from Medtronic plc, of Dublin, Ireland. External device 30A may be, as examples, a programmer, external monitor, or consumer device, e.g., a smartphone, such as the iPhone® by Apple Inc. of Cupertino, Calif.

External device 30A may be used to program commands or operating parameters into ICD 10A for controlling its functioning, e.g., when configured as a programmer for ICD 10A, or when configured to provide timestamp data for calculating a patient-specific body stability score associated with a Sit-To-Stand transition. External device 30A may be used to interrogate ICD 10A to retrieve data, including device operational data as well as physiological data accumulated in IMD memory, such as data associated with a patient-specific body stability score associated with a Sit-To-Stand transition. The interrogation may be automatic, e.g., according to a schedule, or in response to a remote or local user command. Programmers, external monitors, and consumer devices are examples of external devices 30A that may be used to interrogate ICD 10A. Examples of communication techniques used by ICD 10A and external device 30A include radiofrequency (RF) telemetry, which may be an RF link established via Bluetooth®, wireless local area network, wireless wide area network, medical implant communication service (MICS) or other wireless connection.

In some examples, as illustrated in FIG. 1, medical device system 8A may also include a pressure-sensing IMD 50. In the illustrated example, pressure-sensing IMD 50 is implanted in the pulmonary artery of patient 14A. In some examples, one or more pressure-sensing IMDs 50 may additionally or alternatively be implanted within a chamber of heart 16A, or generally at other locations in the circulatory system.

In one example, pressure-sensing IMD 50 is configured to sense blood pressure of patient 14A. For example, pressure-sensing IMD 50 may be arranged in the pulmonary artery and be configured to sense the pressure of blood flowing from the right ventricle outflow tract (RVOT) from the right ventricle through the pulmonary valve to the pulmonary artery. Pressure-sensing IMD 50 may therefore directly measure pulmonary artery diastolic pressure (PAD) of patient 14A. The PAD value is a pressure value that can be employed in patient monitoring. For example, PAD may be used as a basis for evaluating congestive heart failure in a patient.

In other examples, however, pressure-sensing IMD 50 may be employed to measure blood pressure values other than PAD. For example, pressure-sensing IMD 50 may be arranged in right ventricle 28 of heart 14 to sense RV systolic or diastolic pressure, or may sense systolic or diastolic pressures at other locations of the cardiovascular system, such as within the pulmonary artery. As shown in FIG. 1, pressure-sensing IMD 50 is positioned in the main trunk of pulmonary artery 39. In other examples, a sensor, such as pressure-sensing IMD 50 may be either positioned in the right or left pulmonary artery beyond the bifurcation of the pulmonary artery.

Moreover, the placement of pressure-sensing IMD 50 is not restricted necessarily to the pulmonary side of the circulation. The pressure-sensing IMD 50 could potentially be placed in the systemic side of the circulation. For example, under certain conditions and with appropriate safety measures, pressure-sensing IMD 50 could even be placed in the left atrium, left ventricle, or aorta. Additionally, pressure-sensing IMD 50 is not restricted to placement within the cardiovascular system. For example, the pressure-sensing IMD 50 might be placed in the renal circulation. Placement of pressure-sensing IMD 50 in the renal circulation may be beneficial, for example, to monitor the degree of renal insufficiency in the patient based on the monitoring of pressure or some other indication of renal circulation by pressure-sensing IMD 50.

In some examples, pressure-sensing IMD 50 includes a pressure sensor configured to respond to the absolute pressure inside the pulmonary artery of patient 14A. Pressure-sensing IMD 50 may be, in such examples, any of a number of different types of pressure sensors. One form of pressure sensor that may be useful for measuring blood pressure is a capacitive pressure sensor. Another example pressure sensor is an inductive sensor. In some examples, pressure-sensing IMD 50 may also comprise a piezoelectric or piezoresistive pressure transducer. In some examples, pressure-sensing IMD 50 may comprise a flow sensor.

In one example, pressure-sensing IMD 50 comprises a leadless pressure sensor including capacitive pressure sensing elements configured to measure blood pressure within the pulmonary artery. Pressure-sensing IMD 50 may be in wireless communication with ICD 10A and/or external device 30A, e.g., in order to transmit blood pressure measurements to one or both of the devices. Pressure-sensing IMD 50 may employ, e.g., radio frequency (RF) or other telemetry techniques for communicating with ICD 10A and other devices, including, e.g., external device 30A. In another example, pressure-sensing IMD 50 may include a tissue conductance communication (TCC) system by which the device employs tissue of patient 14A as an electrical communication medium over which to send and receive information to and from ICD 10A and/or external device 30A.

Figure 2:
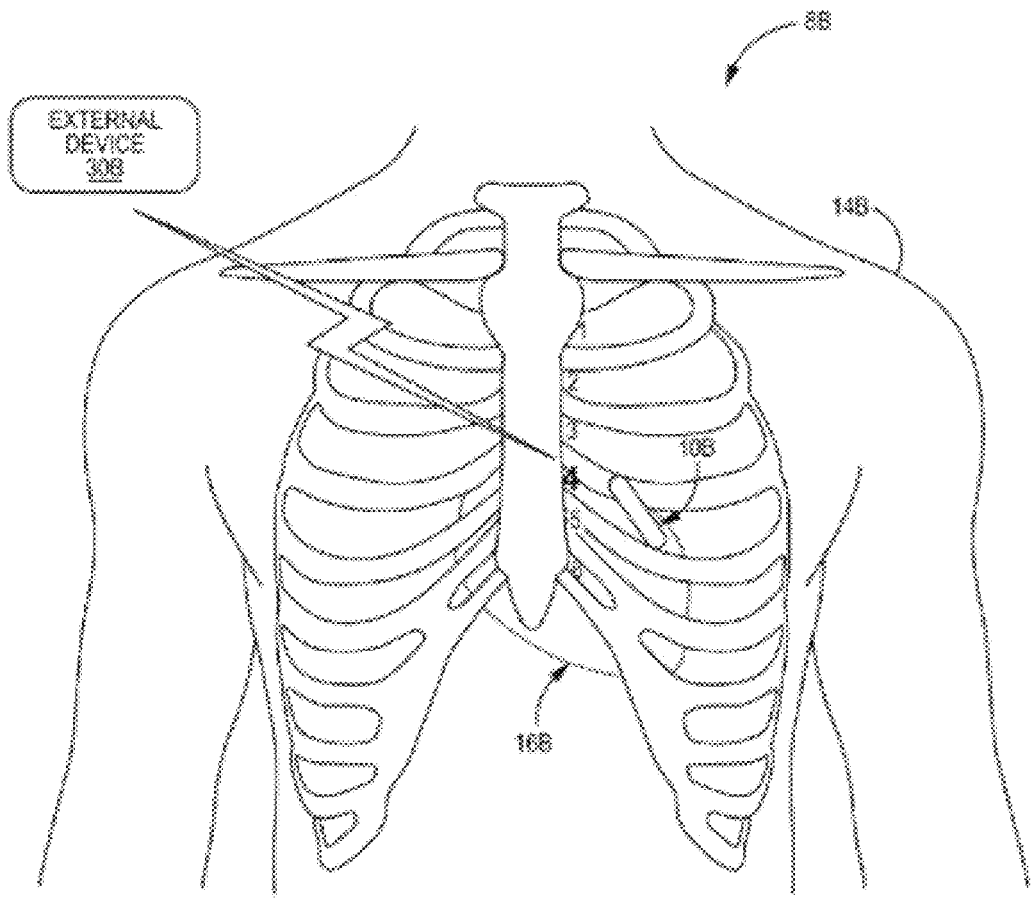
FIG. 2 is a conceptual drawing illustrating another example medical device system in conjunction with a patient.

Medical device system 8A is an example of a medical device system configured for determining body stability of a patient based on accelerometer-generated data. Such techniques as contemplated may be performed by processing circuitry of medical device system 8A, such as processing circuitry of one or both of ICD 10A and external device 30A, individually, or collectively, as discussed in further detail below. Other example medical device systems that may be configured to implement the techniques are described with respect to FIGS. 2-9. Although described herein primarily in the context of implantable medical devices generating signals and, in some examples, delivering therapy, a medical device system that implements the techniques described in this disclosure may additionally or alternatively include an external medical device, e.g., a smartphone, configured to at least generate timestamp data for measuring or determining patient body stability based on accelerometer-generated data FIG. 2 is a conceptual drawing illustrating another example medical device system 8B in conjunction with a patient 14B. Medical device system 8B is another example of a medical device system configured to implement the techniques described herein for determining patient body stability based on accelerometer-generated data. In the illustrated example, medical device system 8B includes an IMD 10B and an external device 30B.

IMD 10B is an insertable cardiac monitor (ICM) capable of sensing and recording cardiac EGM signals from a position outside of heart 16B, and will be referred to as ICM 10B hereafter. Further, ICM 10B is capable of implementing one or more techniques for determining patient body stability based on accelerometer-generated data in accordance with the present disclosure. In some examples, ICM 10B includes or is coupled to one or more additional sensors that generate one or more other physiological signals, such as signals that vary based on patient motion and/or posture, blood flow, or respiration. ICM 10B may be implanted outside of the thorax of patient 14B, e.g., subcutaneously or submuscularly, such as the pectoral location illustrated in FIG. 2. In some examples, ICM 10B may take the form of a Reveal LINQ™ ICM, available from Medtronic plc, of Dublin, Ireland.

External device 30B may be configured in a manner substantially similar to that described above with respect to external device 30A and FIG. 1. External device 30B may wirelessly communicate with ICM 10B, e.g., to program the functionality of the ICM, and to retrieve recorded physiological signals and/or patient parameter values or scores or other data derived from such signals from the ICM. Both ICM 10B and external device 30B include processing circuitry, and the processing circuitry of either or both device may perform the techniques described herein for determining patient body stability based on accelerometer-generated data, as discussed in further detail below.

Although not illustrated in the example of FIG. 2, a medical device system configured to implement the techniques of this disclosure may include one or more implanted or external medical devices in addition to or instead of ICM 10B. For example, a medical device system may include a pressure sensing IMD 50, vascular ICD (e.g., ICD 10A of FIG. 1), extravascular ICD (e.g., ICD 10C of FIGS. 4A-5), or cardiac pacemaker (e.g., IPD 10D of FIGS. 4A-6 or a cardiac pacemaker implanted outside the heart but coupled to intracardiac or epicardial leads). One or more such devices may generate accelerometer signals, and include processing circuitry configured to perform, in whole or in part, the techniques described herein for determining patient body stability based on accelerometer-generated data. The implanted devices may communicate with each other and/or an external device 30, and one of the implanted or external devices may ultimately calculate a patient-specific body stability associated with a Sit-To-Stand transition from at least one of a sagittal axis signal, a vertical axis signal and a transverse axis signal.

Figure 3:
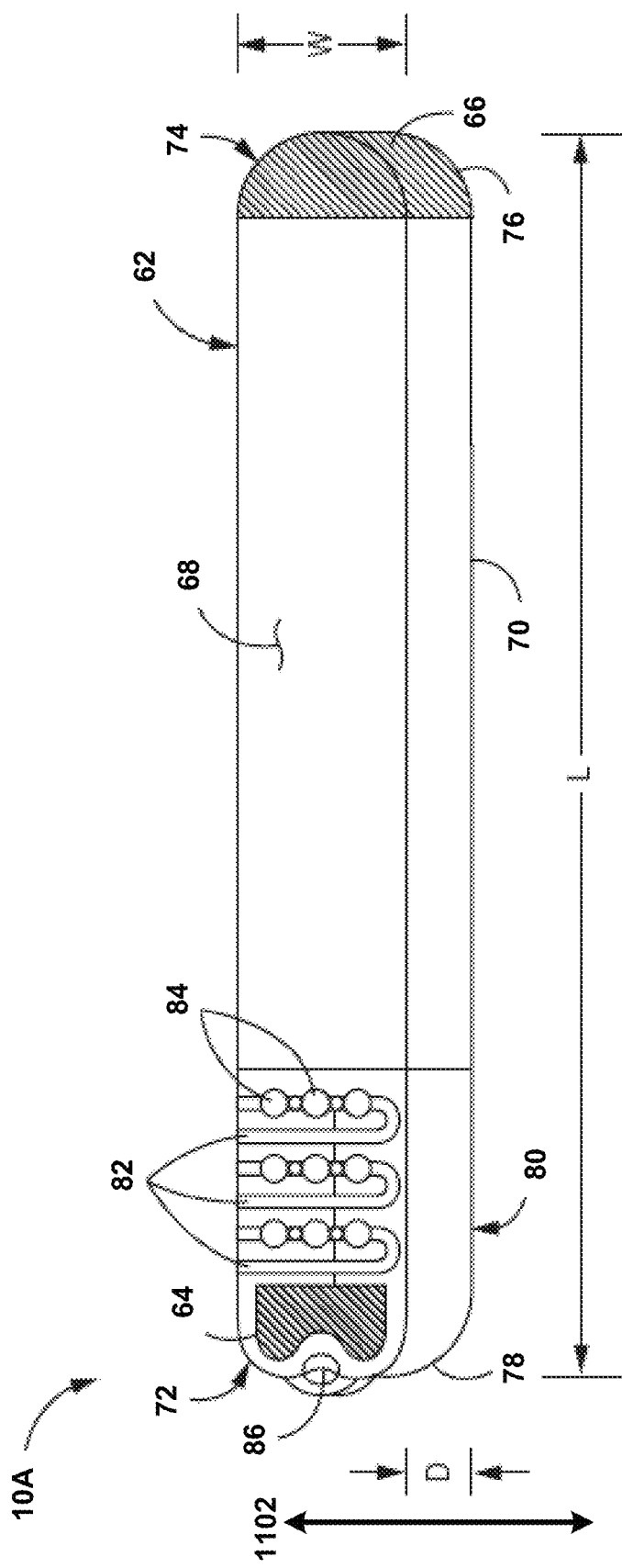
FIG. 3 is a perspective drawing illustrating an example configuration of the implantable cardiac monitor of FIG. 2.

FIG. 3 is a conceptual drawing illustrating an example configuration of ICM 10B. In the example shown in FIG. 3, ICM 300 may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10B and protects the circuitry contained therein from body fluids. Electrical feedthroughs provide electrical connection of electrodes 64 and 66.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—in particular a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10B may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10B may range from 2 mm to 9 mm. In other examples, the depth D of ICM 10B may range from 2 mm to 5 mm and may be any single or range of depths from 2 mm to 9 mm. In addition, ICM 10B according to an example of the present disclosure is has a geometry and size designed for ease of implant and patient comfort. Examples of ICM 10B described in this disclosure may have a volume of three cubic centimeters (cm) or less, 1.5 cubic cm or less or any volume between three and 1.5 cubic centimeters. And, as discussed in further detail below, it is contemplated that an axis of an accelerometer coincident with an axis along D may correspond to a sagittal axis of a patient, and that a sagittal axis signal(s) can be leveraged for measuring or determining patient body stability, as part of a SST (Sit-To-Stand) performance transition for example. This is because 3D accelerometers in the ICM 10B, for example, which is implanted in the chest, and are relatively stationary over the lifetime of the implant. The stationary chest location presents an opportunity to monitor changes in the upper body that occur during various activities. As a patient gets in and out of a chair for example the upper body has a reproducible motion (similar to a "bowing" motion) that may be identified with signals produced by the accelerometers.

In the example shown in FIG. 3, once inserted within the patient, the first major surface 68 faces outward, toward the skin of the patient while the second major surface 70 is located opposite the first major surface 68. In addition, in the example shown in FIG. 3, proximal end 72 and distal end 74 are rounded to reduce discomfort and irritation to surrounding tissue once inserted under the skin of the patient. ICM 10B, including instrument and method for inserting ICM 10B is described, for example, in U.S. patent application Ser. No. 14/204,227 now published as U.S. Publication No. 2014/0276928, titled "SUBCUTANEOUS DELIVERY TOOL," filed Mar. 11, 2014, claiming priority to U.S. Provisional Patent Application 61/788,940, the entirety of which is incorporated herein by reference.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 82 to another medical device, which may be another implantable device or an external device, such as external device 30B. In some example, electrodes 64 and 66 may additionally or alternatively be used for sensing any biopotential signal of interest, which may be, for example, an EGM, EEG, EMG, or a nerve signal, from any implanted location.

In the example shown in FIG. 3, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 3, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64.

The various electrode configurations allow for configurations in which proximal electrode 64 and distal electrode 66 are located on both first major surface 68 and second major surface 70. In other configurations, such as that shown in FIG. 3, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10B may include electrodes on both major surface 68 and 70 at or near the proximal and distal ends of the device, such that a total of four electrodes are included on ICM 10B. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10B to transmit and/or receive data. In other examples, integrated antenna 82 may be formed on the opposite major surface as proximal electrode 64, or may be incorporated within the housing 82 of ICM 10B. In the example shown in FIG. 3, anti-migration projections 84 are located adjacent to integrated antenna 82 and protrude away from first major surface 68 to prevent longitudinal movement of the device. In the example shown in FIG. 3, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 3 header assembly 80 includes suture hole 86, which provides another means of securing ICM 10B to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10B.

Figure 4A:
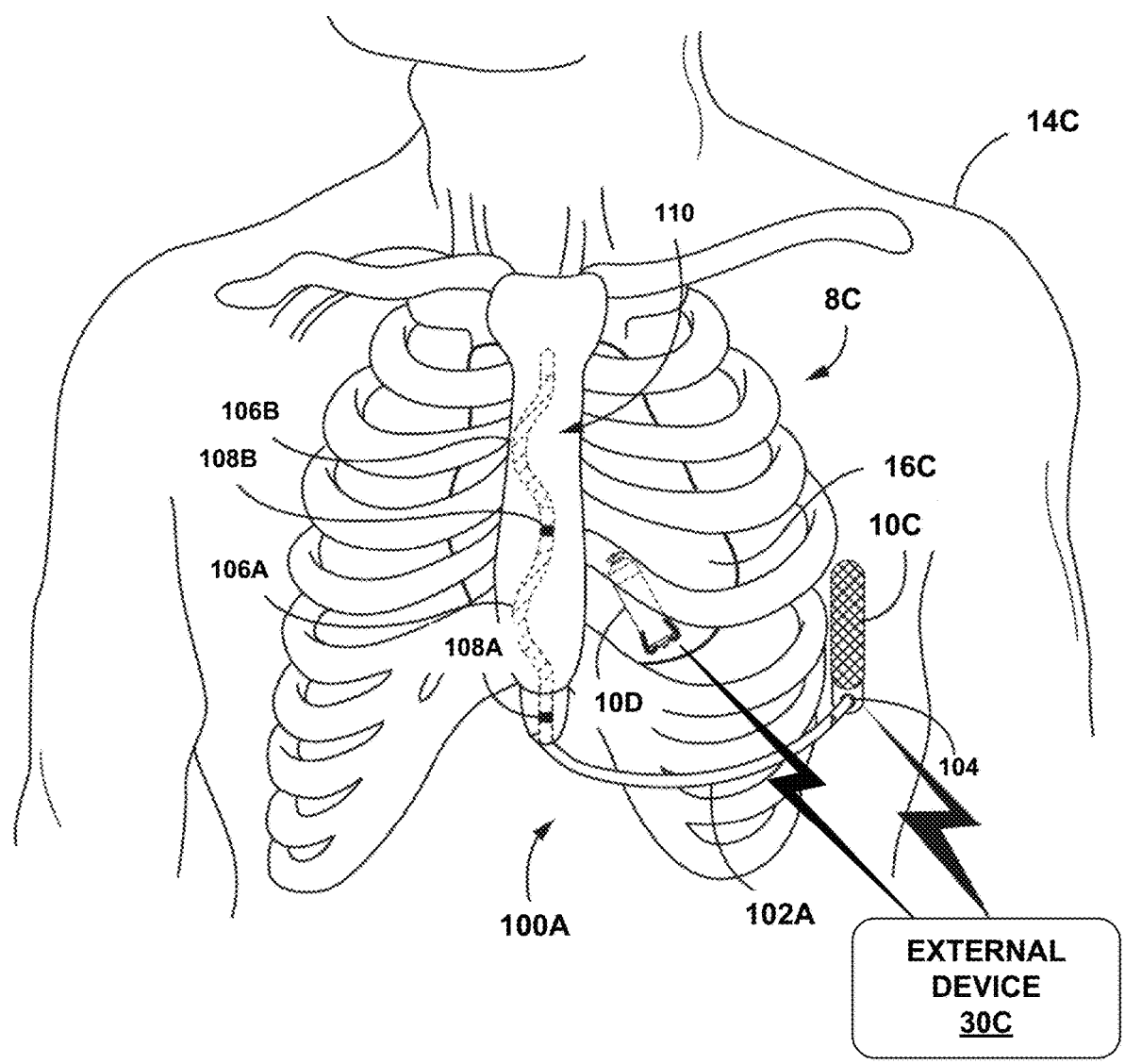
FIGS. 4A-4C is a front-view, side-view, and top-view conceptual drawings, respectively, illustrating another example medical device system in conjunction with a patient.
Figure 4B:
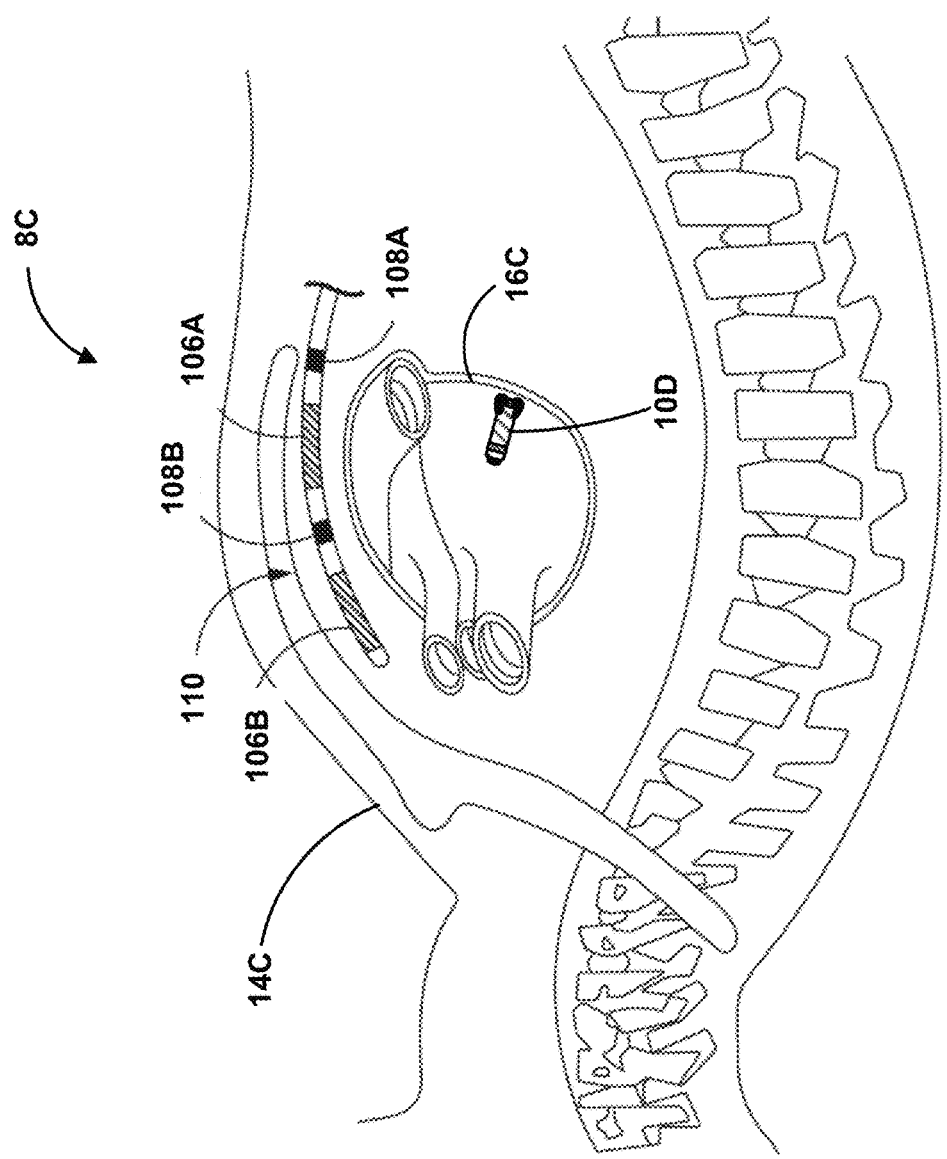
Figure 4C:
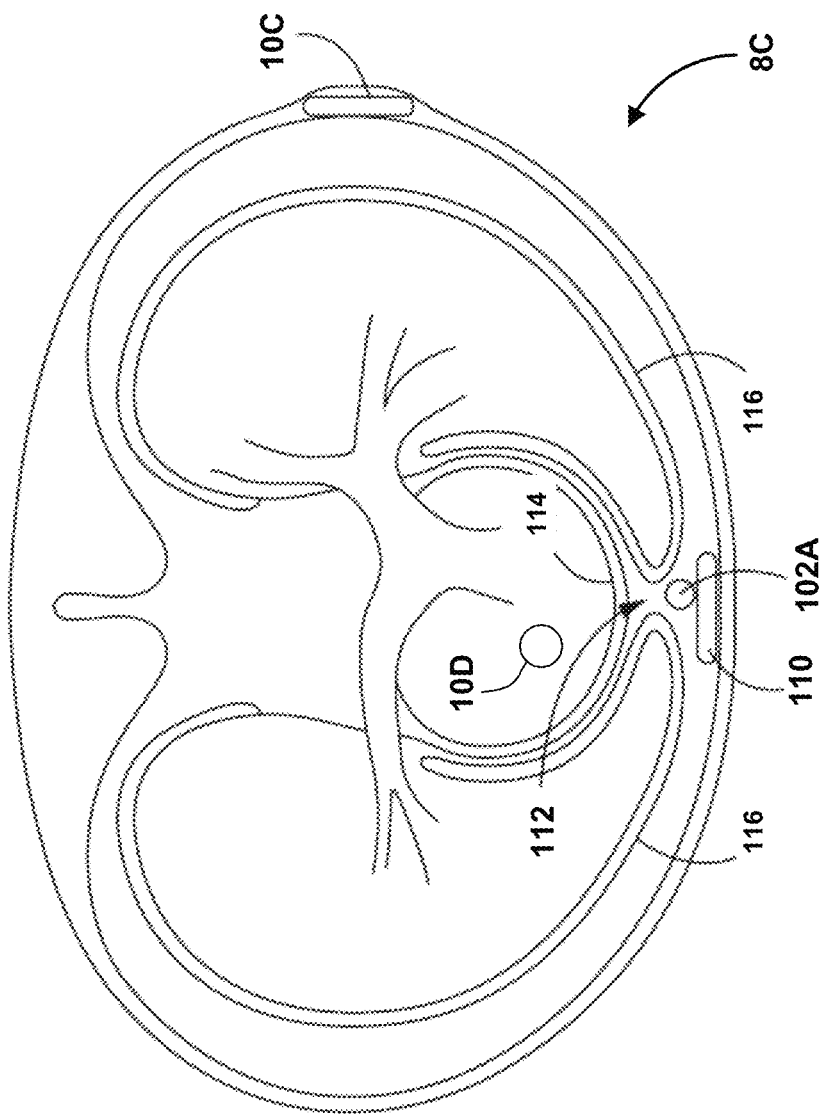

FIGS. 4A-4C are front-view, side-view, and top-view conceptual drawings, respectively, illustrating another example medical device system 8C in conjunction with a patient 14C. Medical device system 8C is another example of a medical device system configured to implement the techniques described herein for determining patient body stability based on accelerometer-generated data.

In the illustrated example, medical device system 8C includes an extracardiovascular ICD system 100A implanted within a patient 14C. ICD system 100A includes an IMD 10C, which is an ICD and is referred to hereafter as ICD 10C, connected to at least one implantable cardiac defibrillation lead 102A. ICD 10C is configured to deliver high-energy cardioversion or defibrillation pulses to a patient's heart 16C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between defibrillation electrodes 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the defibrillation electrode sections 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s) 108"), located along the distal portion of defibrillation lead 102A. In the example illustrated in FIG. 4A and FIG. 4B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the defibrillation electrode sections 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10D and ICD 10C is described in commonly-assigned U.S. Pat. No. 8,744,572 titled, "SYSTEMS AND METHODS FOR LEADLESS PACING AND SHOCK THERAPY" which issued on Jun. 3, 2014, the entire content of which is incorporated by reference herein.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 30C may allow a user to program any coefficients, weighting factors, or techniques for determining difference metrics, scores, and/or thresholds, or other data described herein as being used by a medical device system to determine patient body stability based on accelerometer-generated data. As another example, external device 30C may be used to program commands or operating parameters into ICD 10C for controlling its functioning. External device 30C may be used to interrogate ICD 10C to retrieve data, including device operational data as well as physiological data accumulated in IMD memory, such as data associated with a patient-specific body stability associated with a Sit-To-Stand transition. ICD 10C may be configured to implement the various features or aspects of the present disclosure for determining patient body stability based on accelerometer-generated data.

Medical device system 10D is an example of a medical device system configured for determining patient body stability based on accelerometer-generated data. Such techniques as contemplated may be performed by processing circuitry of medical device system 10D, such as processing circuitry of one or both of system 10D and external device 30C, individually, or collectively, as discussed in further detail below following a description provided in connection with FIGS. 10 and 11. Other example medical device systems that may be configured to implement the techniques are described below.

Figure 5:
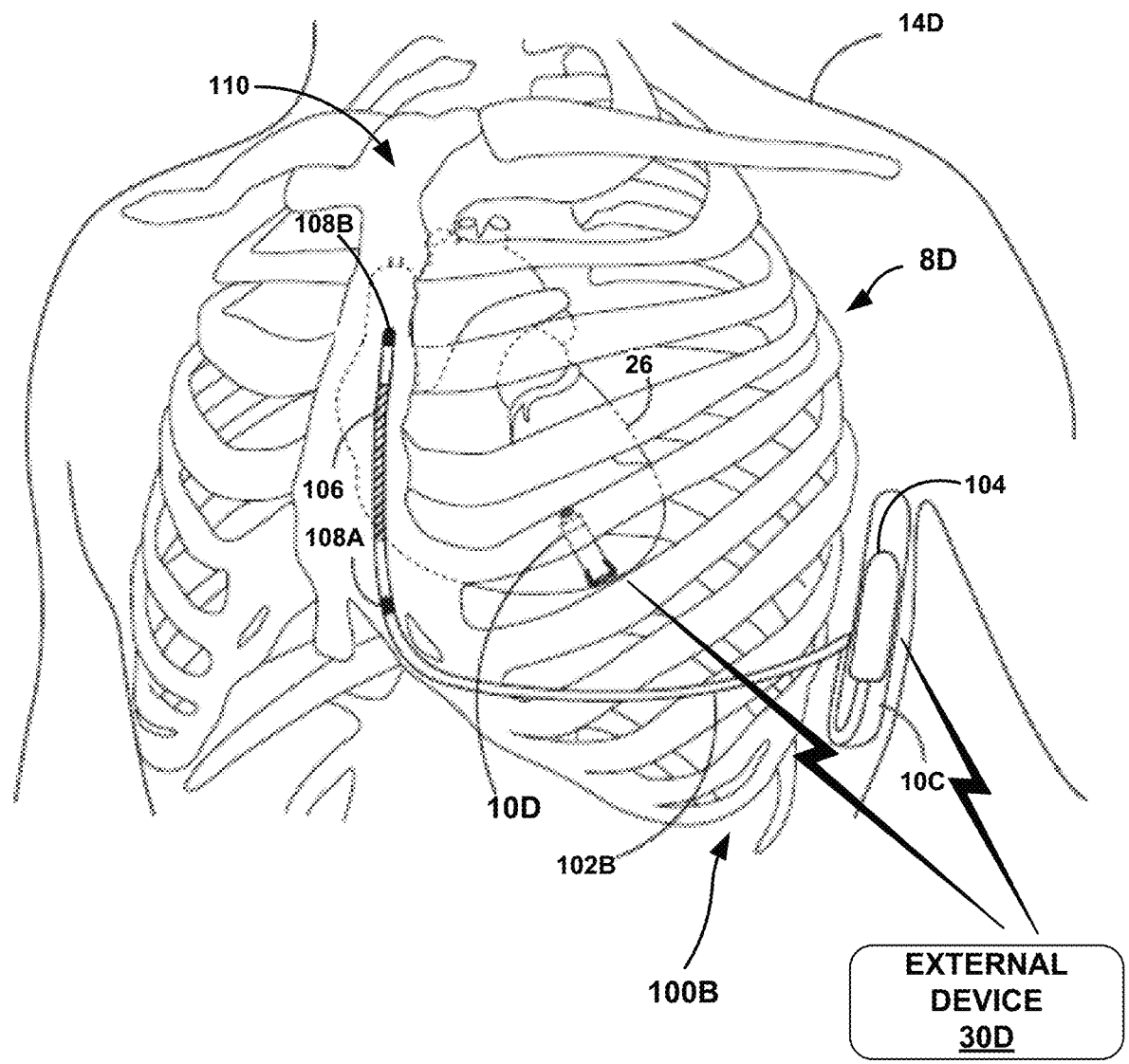
FIG. 5 is a conceptual drawing illustrating another example medical device system in conjunction with a patient.

FIG. 5 is a conceptual drawing illustrating another example medical device system 8D that includes an extra-cardiovascular ICD system 100B and IPD 10D implanted within a patient. Medical device system 8B may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A-4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., defibrillation electrodes 106A and 106B as illustrated in the example of FIGS. 4A-4C.

Medical device system 8D is an example of a medical device system configured for determining patient body stability based on accelerometer-generated data. Such techniques as contemplated may be performed by processing circuitry of medical device system 8D, such as processing circuitry of one or both of system 8D and external device 30D, individually, or collectively, as discussed in further detail below.

Figure 6:
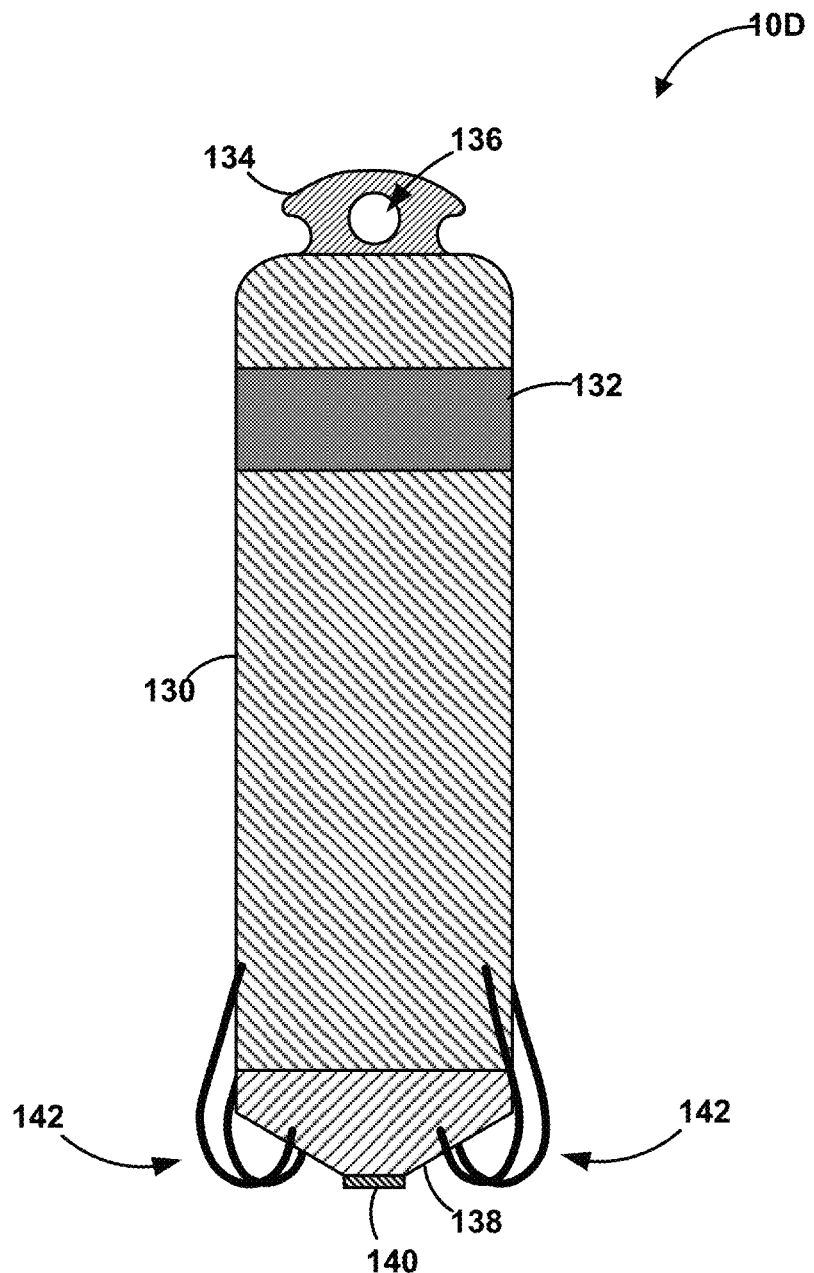
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140) to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 144 may be provided on one end of case 130 to enable tethering or extraction of IPD 10D. For example, a suture or other device may be inserted around flange 144 and/or through opening 146 and attached to tissue. In this manner, flange 144 may provide a secondary attachment structure to tether or retain IPD 10D within heart 16C (or 16D) if fixation mechanisms 142 fail. Flange 144 and/or opening 146 may also be used to extract IPD 10D once the IPD needs to be explanted (or removed) from patient 14D if such action is deemed necessary.

Referring back to FIGS. 4A-5, medical device systems 8C and 8D are examples of medical device systems configured for determining patient body stability based on accelerometer-generated data. Such techniques may be performed by processing circuitry of medical device system 8C or 8D, such as processing circuitry of one or more of ICD 10C, IPD 10D, and external device 30C or 30D, individually, or collectively. Although the example medical devices systems 8C and 8D of FIGS. 4A-5 are illustrated as including both ICD 10C and IPD 10D, other examples may include only one of ICD 10C or IPD 10D, alone, or in combination with other implanted or external devices.

Figure 7:
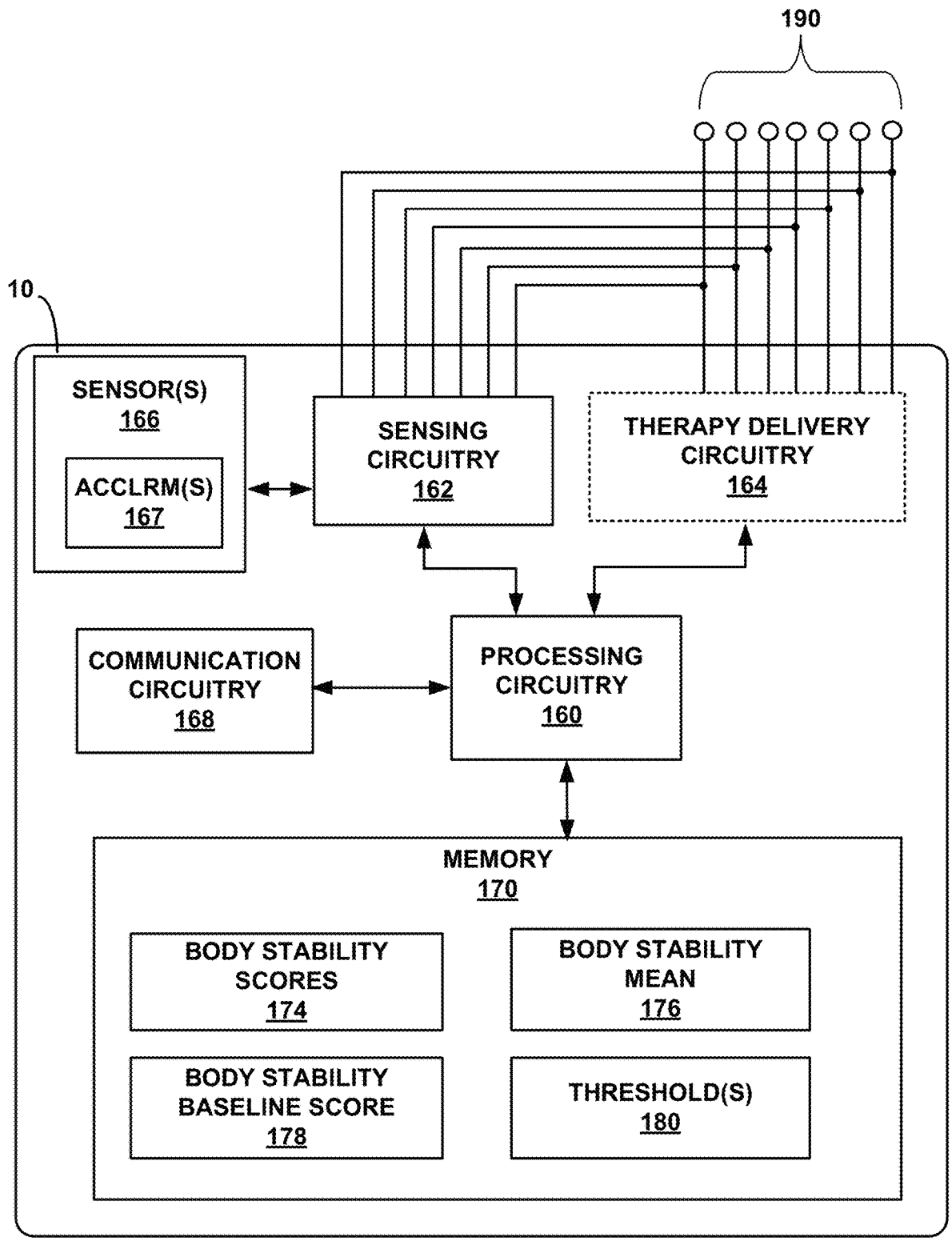
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement the techniques for determining patient body stability based on accelerometer-generated data described in this disclosure. In the illustrated example, IMD 10 includes processing circuitry 160 and an associated memory 170, sensing circuitry 162, therapy delivery circuitry 164, one or more sensors 166, and communication circuitry 168. However, ICD 10A, ICM 10B, ICD 10C, and IPD 10D need not include all of these components, or may include additional components. For example, ICM 10B may not include therapy delivery circuitry 164, in some examples (illustrated by intermittent line).

Memory 170 includes computer-readable instructions that, when executed by processing circuitry 160, cause IMD 10 and processing circuitry 160 to perform various functions attributed to IMD 10 and processing circuitry 160 herein (e.g., calculate a patient-specific body stability associated with a Sit-To-Stand transition from at least one of the sagittal axis signal, the vertical axis signal and the transverse axis signal). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 7 may correspond to, for example: electrodes 12, 22, 24, 26, 28, 44, and 44 of ICD 10A (FIG. 1); electrodes 64 and 66 of ICM 10B (FIG. 3); electrodes 106, 108, and one or more housing electrodes of ICD 10C (FIGS. 4A-5); or electrodes 132 and 140 of IPD 10D (FIG. 6).

Sensing circuitry 162 monitors signals from a selected two or more of electrodes 190 in order to monitor electrical activity of heart 26, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 26. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMD 10 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 160 may utilize all or a subset of the rule-based detection methods described in U.S. Pat. No. 5,545,186 entitled "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 entitled "PRIORITIZED RULE BASED METHOD AND APPARATUS FOR DIAGNOSIS AND TREATMENT OF ARRHYTHMIAS," which issued on May 26, 1998. U.S. both of which are incorporated herein by reference in their entireties. However, other arrhythmia detection methodologies, such as those methodologies that utilize timing and morphology of the electrocardiogram, may also be employed by processing circuitry 160 in other examples.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 26. As another example, processing circuitry 160 may analyze the digitized cardiac electrogram signal to identify and measure a variety of morphological features of the signal.

In some examples, sensing circuitry 162 is configured to sense other physiological signals of patient. For example, sensing circuitry 162 may be configured to sense signals that vary with changing thoracic impedance of patient 14. The thoracic impedance may vary based on fluid volume or edema in patient 14.

Sensing circuitry 162 may use any two or more of electrodes 190 to sense thoracic impedance. As the tissues within the thoracic cavity of patient 14 change in fluid content, the impedance between two electrodes may also change. For example, the impedance between a defibrillation coil electrode (42, 44, 106) and the housing electrode may be used to monitor changing thoracic impedance.

In some examples, processing circuitry 160 measured thoracic impedance values to determine a fluid index. As more fluid is retained within patient 14, e.g., edema increases, and the thoracic impedance decreases or remains relatively high, the fluid index increases. Conversely, as the thoracic impedance increases or remains relatively low, the fluid index decreases. An example system for measuring thoracic impedance and determining a fluid index is described in U.S. Pat. No. 8,255,046 entitled "DETECTING WORSENING HEART FAILURE BASED ON IMPEDANCE MEASUREMENTS," which issued on Aug. 28, 2012 and is incorporated herein by reference in its entirety.

The thoracic impedance may also vary with patient respiration. In some examples, processing circuitry 160 may determine values of one or more respiration-related patient parameters based on thoracic impedance sensed by sensing circuitry 162. Respiration-related patient parameters may include, as examples, respiration rate, respiration depth, or the occurrence or magnitude of dyspnea or apneas.

The magnitude of the cardiac electrogram may also vary based on patient respiration, e.g., generally at a lower frequency than the cardiac cycle. In some examples, processing circuitry 160 and/or sensing circuitry 162 may filter the cardiac electrogram to emphasize the respiration component of the signal. Processing circuitry 160 may analyze the filtered cardiac electrogram signal to determine values of respiration-related patient parameters.

In the example of FIG. 7, IMD 10 includes one or more sensors 166 coupled to sensing circuitry 162. Although illustrated in FIG. 7 as included within IMD 10, one or more of sensors 166 may be external to IMD 10, e.g., coupled to IMD 10 via one or more leads, or configured to wirelessly communicate with IMD 10. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers 167, e.g., one or more 3-axis accelerometers. Signals generated by the one or more accelerometers 167, such as one or more of a sagittal axis signal, a vertical axis signal and a transverse axis signal, may be indicative of, as examples, gross body movement (e.g., activity) of patient 14, patient posture, heart sounds or other vibrations or movement associated with the beating of the heart, or coughing, rales, or other respiration abnormalities. In some examples, sensors 166 include one or more microphones configured to detect heart sounds or respiration abnormalities, and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals.

In some examples, sensors 166 include one or more pressure sensors that transduce one or more signals indicative of blood pressure, and processing circuitry 160 determines one or more patient parameter values based on the pressure signals. Patient parameter values determined based on pressure may include, as examples, systolic or diastolic pressure values, such as pulmonary artery diastolic pressure values. In some examples, a separate pressure-sensing IMD 50 includes one or more sensors and sensing circuitry configured to generate a pressure signal, and processing circuitry 160 determines patient parameter values related to blood pressure based on information received from IMD 50.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

In some examples, processing circuitry 160 monitors for Sit-to-Stand transitions and determines a respective body stability score for each Sit-to-Stand transition. Details on how to determine a Sit-to-Stand transition is occurring based on an accelerometer signal can be found in commonly-assigned U.S. patent application Ser. No. 15/607,945, titled, "ACCELEROMETER SIGNAL CHANGE AS A MEASURE OF PATIENT FUNCTIONAL STATUS," filed May 25, 2017, now published as US Patent Application Publication No. US 2018/0035924 A1 and claiming the benefit of Provisional Application No. 62/370,138, filed on Aug. 2, 2016, the entire content of which is incorporated by reference herein. The determined body stability scores 174 may be stored in memory 170.

In some examples, processing circuitry 160 may determine a body stability score based upon the length of time it takes from the Sit-to-Stand transition until the first step is taken by patient 14. Details on how to determine when a step is taken can be found in commonly-assigned U.S. patent application Ser. No. 15/603,776, titled, "STEP DETECTION USING ACCELEROMETER AXIS," filed May 24, 2017, now published as US Patent Application Publication No. US 2018/0035920 A1 and claiming the benefit of Provisional Application No. 62/370,102, filed on Aug. 2, 2016, the entire content of which is incorporated by reference herein.

The measurement of the length of time it takes from the Sit-to-Stand transition until the first step may begin at the beginning of the Sit-to-Stand transition, at the end of the Sit-to-stand transition, or anywhere therebetween, for instance at the peak of the signal indicative of the Sit-to-Stand transition. The measurement of the length of time it takes from the Sit-to-Stand transition until the first step may end at the beginning of the first step, at the end of the first step, or anywhere therebetween, for instance at the peak of the signal indicative of the first step. In this example, the body stability score may be a unit of time, for example seconds.

In other examples, processing circuitry 160 may determine a body stability score based upon the number of peaks and/or valleys in an accelerometer signal during a predetermined period of time, for example several seconds, such as 5 seconds. This predetermined period of time is associated with the Sit-to-Stand transition and may begin any time during or immediately after the Sit-to-Stand transition. Multiple peaks and/or valleys may indicate patient 14 is swaying. In these examples, the body stability score may be a simple count of peaks and/or valleys in the accelerometer signal.

In other examples, processing circuitry 160 may determine a body stability score by measuring the amplitude of a peak to valley in an accelerometer signal during a Sit-to-Stand transition. In these examples, the body stability score may be measured in g's (or forces of gravity).

In other examples, processing circuitry 160 may determine a body stability score by measuring the time it takes for a peak to valley in an accelerometer signal to reach a predetermined amplitude threshold, for example 0.2 g. In these examples, the body stability score may be a unit of time, for example seconds or fractions thereof.

In other examples, processing circuitry 160 may determine a body stability score by measuring a slope of a Sit-to-Stand transition in an accelerometer signal. In these examples, the body stability score may be measured in degrees.

In some examples, processing circuitry 160 may determine a body stability score based upon any combination of: 1) the length of time it takes from the Sit-to-Stand transition until the first step is taken by patient 14; 2) the number of peaks and/or valleys in an accelerometer signal during a predetermined period of time; 3) the amplitude of a peak to valley in an accelerometer signal during a Sit-to-Stand transition; 4) the time it takes for a peak to valley in an accelerometer signal to reach a predetermined amplitude threshold; and 5) the slope of Sit-to-Stand transition in an accelerometer signal. Each of the measures used to determine the body stability score may be equally weighted or may be unequally weighted. In the event, more than one unit of measure (e.g., time, count and g's) is used, processing circuitry may convert the units of measure by scaling each and combining them into to a raw score.

Communication circuitry 168 includes any suitable hardware, firmware, software or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The clinician may also program parameters of IMD 10 using external device 30 or another local or networked computing device. In some examples, the clinician may select the method used to quantify the Body stability scores.

Figure 8:
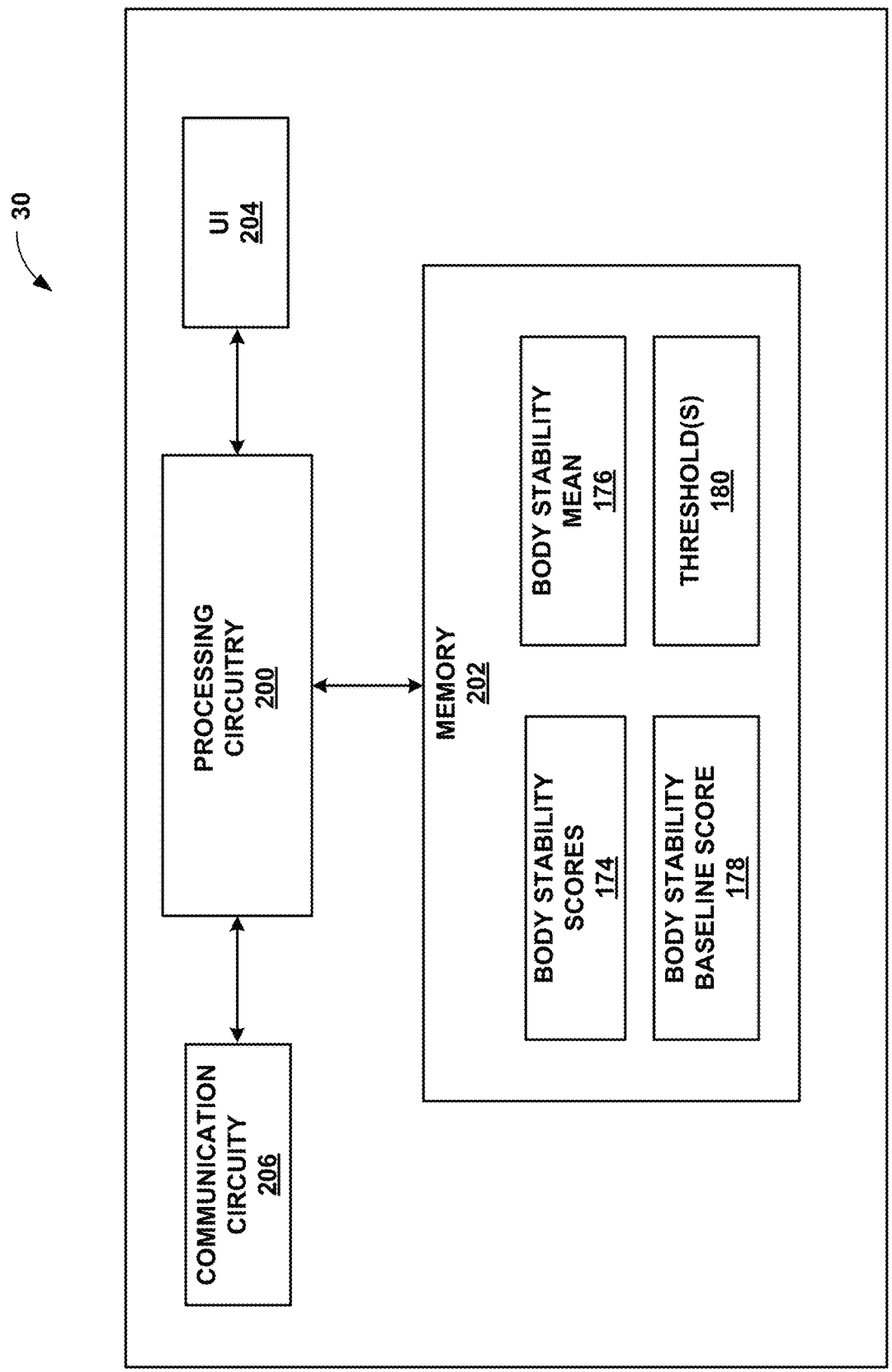
FIG. 8 is a functional block diagram illustrating an example configuration of an external device configured to communicate with one or more implantable medical devices.

FIG. 8 is a functional block diagram illustrating an example configuration of an external device 30 configured to communicate with one or more IMDs 10. In the example of FIG. 8, external device 30 includes processing circuitry 200, memory 202, user interface (UI) 204, and communication circuitry 206. External device 30 may correspond to any of external devices 30A-30D described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., a smartphone running a mobile application that enables external device 30 to program and/or interrogate IMD 10. In some examples where external device 30 is a smart phone, external device 30 may include a mobile application to facilitate interaction with IMD 10, for example, as described in commonly-assigned U.S. patent application Ser. No. 15/607,945, titled, "MOBILE APPLICATION TO PROMPT PHYSICAL ACTION TO MEASURE PHYSIOLOGIC RESPONSE IN IMPLANTABLE DEVICE," filed May 30, 2017, now published as US Patent Application Publication No. US 2018/0035956 A1 and claiming the benefit of Provisional Application No. 62/370,146, filed on Aug. 2, 2016, the entire content of which is incorporated by reference herein. the entire content of which is incorporated by reference herein.

In some examples, a user of external device 30 may be clinician, physician, heath care giver, patient, family member of the patient or friend of the patient. In some examples, a user uses external device 30 to select or program any of the values for operational parameters of IMD 10, e.g., for measuring or determining patient body stability based on accelerometer-generated data. In some examples, a user uses external device 30 to receive data collected by IMD 10, such as body stability scores 174 or other operational and performance data of IMD 10. The user may also receive alerts provided by IMD 10 that indicate that an acute cardiac event, e.g., ventricular tachyarrhythmia, is predicted. The user may also receive alerts that the patient may be more likely to fall or that the patient needs attention due to deterioration of the patient's body stability. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive physiological signals generated by one or more IMDs 10 and determine body stability scores 174 and/or may receive body stability scores 174 from one or more IMDs 10. Processing circuitry 200 may determine body stability mean 176, body stability baseline score 178, and thresholds 180 in the manner described herein with respect to processing circuitry 160 of IMD 10 for determining patient body stability based on accelerometer-generated data.

Figure 9:
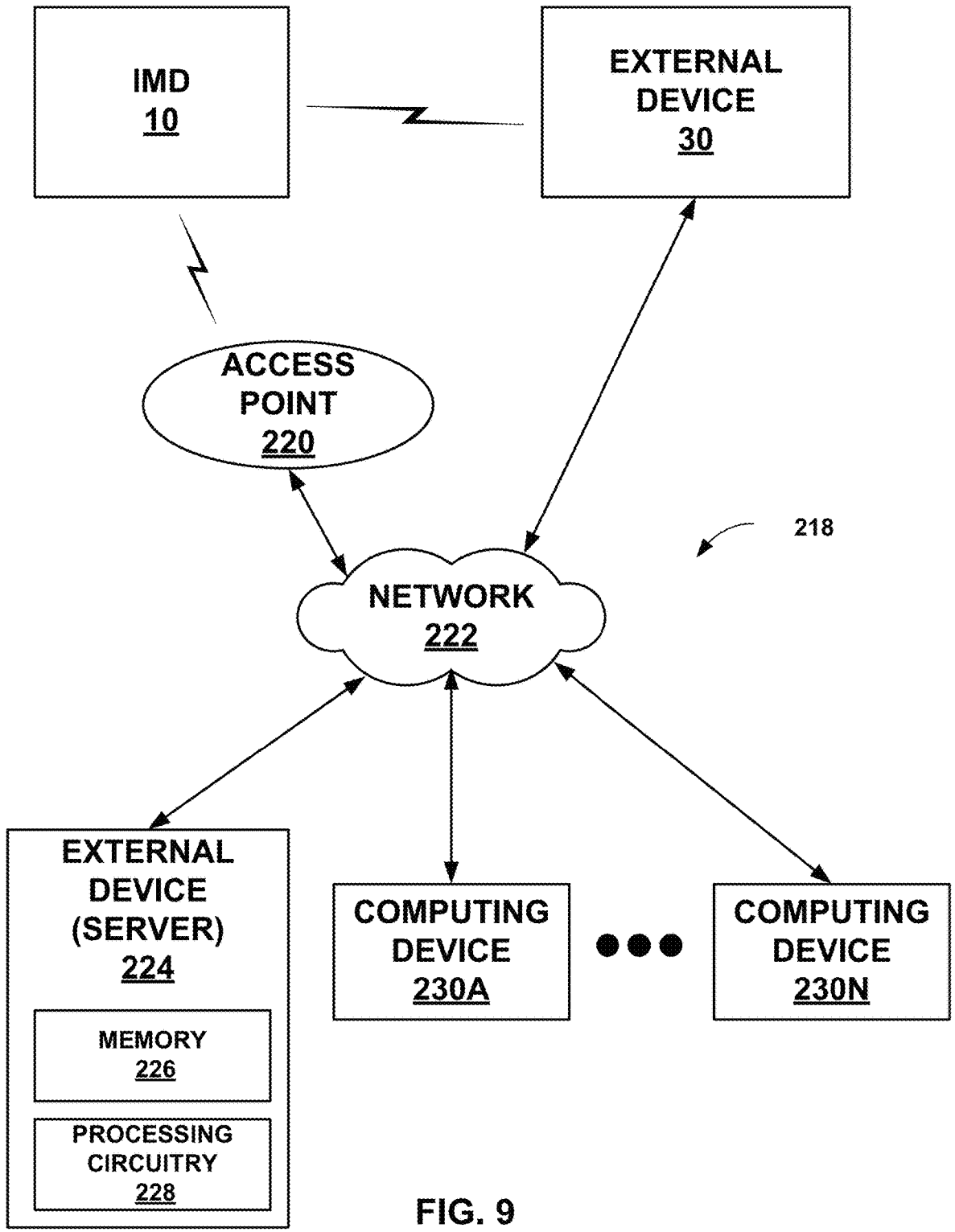
FIG. 9 is a functional block diagram illustrating an example system that includes remote computing devices, such as a server and one or more other computing devices, that are connected to an implantable medical device and/or external device via a network.

FIG. 9 is a functional block diagram illustrating an example system that includes external computing devices, such as a server 224 and one or more other computing devices 230A-230N, that are coupled to IMD 10 and external device 30 via a network 222. In this example, IMD 10 may use its communication module 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, body stability scores 174, body stability mean 176, body stability baseline score 178, thresholds 180, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, relating to determining patient body stability based on accelerometer-generated data. In the example of FIG. 9, server 224 includes a memory 226 to store signals or body stability scores 174 received from IMD 10 and/or external device 30, and processing circuitry 228, which may be configured to provide some or all of the functionality ascribed to processing circuitry 160 of IMD 10 and processing circuitry 200 of external device 30 herein. For example, processing circuitry 228 may determine body stability scores 174, and/or may receive body stability scores 174 from one or more IMDs 10. Processing circuitry 228 may determine body stability mean 176, body stability baseline score 178, thresholds 180 in the manner described above with respect to processing circuitry 160 of IMD 10 for determining patient body stability based on accelerometer-generated data.

As mentioned above, a medical device system according to certain features or aspects of this disclosure includes accelerometer circuitry configured to generate a number of signals including a sagittal (frontal) axis signal, as well as processing circuitry configured to calculate a patient-specific body stability score associated with a Sit-To-Stand transition from the sagittal axis signal. Such an implementation may, among other things, provide an objective measure of change (or not) in well-being to help guide therapies, because a patient-specific body stability score associated with a Sit-To-Stand transition can help determine whether health is improving, declining, or stable.

Figure 10:
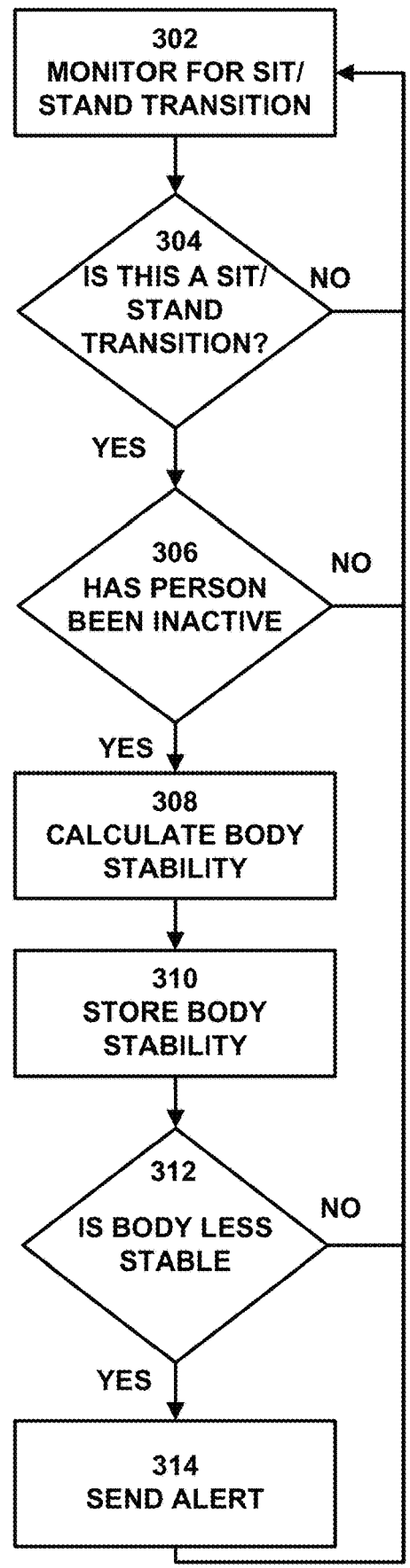
FIG. 10 is a flowchart illustrating a first example method for determining patient body stability score based on accelerometer-generated data in accordance with the disclosure.

FIG. 10 is a flowchart illustrating a first example for determining patient body stability based on accelerometer-generated data in accordance with this disclosure. This example may be implemented by any one of the implantable medical devices discussed above in connection with FIGS. 1-9, because each one of the same is configured to include at least one accelerometer (i.e., accelerometer circuitry), as well as communication and processing circuitry (see FIG. 7 and corresponding description) to facilitate determining patient body stability based on accelerometer-generated data. This example may also be implemented by an external medical device or any implantable or external device having at least one accelerometer.

For example, and with reference to ICM 10B of FIG. 2, ICM 10B may monitor patient 14 for a Sit-to-Stand transition (302). ICM 10B may utilize an on-board accelerometer signal to determine a Sit-to-Stand transition is occurring. This signal may be one or more of a sagittal axis signal, a vertical axis signal and a transverse axis signal.

ICM 10B may then determine whether a Sit-to-Stand transition has occurred (304). If ICM 10B determines a Sit-to-Stand transition has not occurred, ICM 10B may continue to monitor for a Sit-to-Stand transition (302). If ICM 10B determines Sit-to-Stand transition has occurred, ICM 10B may determine if patient 14 has been inactive for a predetermined period of time prior to the Sit-to-Stand transition (306). ICM 10B may make this determination based on a signal from an activity sensor. In some examples, the activity sensor is the accelerometer within ICB 10B or whichever medical device is performing the techniques of this disclosure. In some examples, processing circuitry 160 determines a number of activity counts based on one or more accelerometer signals exceeding one or more thresholds 180 and uses the number of activity counts to determine if the patient has been inactive for the predetermined period of time. The activity counts used to determine if the patient has been inactive for the predetermined period of time may be a total, mean, or median number of counts during the period. In some examples, ICM 10B may determine if patient 14 has been inactive by determining patient 14 has not taken a step by monitoring the accelerometer signal for an indication that a step has been taken as discussed above.

If ICM 10B does not determine that patient 14 has been inactive for at least a predetermined period of time prior to the Sit-to-Stand transition, ICM 10B may ignore the Sit-to-Stand transition and continue to monitor for another Sit-to-Stand transition (302). The predetermined period of time may be programmable by external device 30 for example, or may be fixed. In some examples, the predetermined period of time may be several minutes, such as six minutes. ICM 10B may ignore the Sit-to-Stand transition shortly after a period in which patient 14 is active because recent activity may decrease the likelihood of patient 14 body stability being worse than normal or the measurement regarding the Sit-to-Stand transition may not be as comparable with other measurements due to it not being consistent with less inactive times. By ignoring the Sit-to-Stand transition shortly after a period in which patient 14 is active, ICM 10B may save battery power and may preserve a data set of Sit-to-Stand transitions that is more indicative of a measure of body stability issues. Alternatively, ICM 10B may not determine if patient 14 has been inactive for a predetermined period of time prior to the Sit-to-Stand transition skipping diamond 306 and proceeding directly from diamond 304 to box 308 of FIG. 10.

If patient 14 has been inactive for at least a pre-determined period of time prior to the Sit-to-Stand transition, ICM 10B may determine a body stability score (308). The body stability score may be a representation of the body stability of patient 14 during the Sit-to-Stand transition. In some examples, processing circuitry 160 may determine a body stability score based upon the length of time it takes from the Sit-to-Stand transition until the first step is taken by patient 14. In other examples, processing circuitry 160 may determine a body stability score based upon the number of peaks and/or valleys in an accelerometer signal during a predetermined period of time, for example, 5 seconds. In other examples, processing circuitry 160 may determine a body stability score by measuring the amplitude of a peak to valley in an accelerometer signal during a Sit-to-Stand transition, for example 0.6 g. In other examples, processing circuitry 160 may determine a body stability score by measuring the time it takes for a peak to valley in an accelerometer signal to reach a predetermined amplitude threshold, for example 0.1 g or 0.2 g. In other examples, processing circuitry 160 may determine a body stability score by measuring a slope of an accelerometer signal, as a steep slope may be more indicative of a stable body and a gradual slope may be more indicative of an instable body. In some examples, processing circuitry 160 may determine a body stability score based upon any combination of: 1) the length of time it takes from the Sit-to-Stand transition until the first step is taken by patient 14; 2) the number of peaks and/or valleys in an accelerometer signal during a predetermined period of time; 3) the amplitude of a peak to valley in an accelerometer signal during a Sit-to-Stand transition; 4) the time it takes for a peak to valley in an accelerometer signal to reach a predetermined amplitude threshold; and 5) the slope of an accelerometer signal during a Sit-to-Stand transition.

ICM 10B may then store the body stability score in body stability scores 174 in memory 170 for example (310). ICM 10B may compare the determined body stability score against a body stability baseline score. ICM 10B may calculate the body stability baseline score by determining body stability scores for a period of time, for example one week, and then calculating a mean, median or mode of those body stability scores that were determined during that period of time. In some examples, ICM 10B may discard outlier score(s) before calculating the mean, median or mode. ICM 10B may store this mean, median or mode as the body stability baseline score 178 in memory 202, for example. Alternatively, body stability baseline score 178 may be input into ICM 10B by external device 30. Body stability baseline score 178 may be fixed or may be altered over time. For example, ICM 10B may or may not calculate new body stability scores 174 into body stability baseline score 178.

ICM 10B may then compare the body stability score against body stability baseline score 178 (312). If the body stability score deviates by at least a predetermined amount from body stability baseline score 178 in a manner indicative of less body stability (e.g., it took longer to take the first step after a Sit-to-Stand transition), then ICM 10B may send an alert (314) to a recipient, such as physician, clinician, health care worker, patient 14, a family member of patient 14, a friend of patient 14 or the like. In some examples, the predetermined amount may be on the order of a 50% deviation from the baseline and may be indicative of an acute change in the body stability of patient 14. For example, if the body stability score is the time it takes patient 14 to take the first step after a Sit-to-Stand transition and body stability baseline score is 4 seconds, if patient 14 now is taking 6 seconds from the Sit-to-Stand transition to take their first step, ICM 10B may send the alert. In some examples, ICM 10B may send the alert only after measuring that the body stability score(s) deviates by at least the predetermined amount from body stability baseline score 178 for two consecutive days.

In some examples, ICM 10B may monitor for chronic changes in body stability. For example, ICM 10B may determine a slope of change in body stability scores 174 over time. If the slope of body stability scores 174 deviate from zero in a significant way over a longer period of time, two weeks for example, ICM 10B may send an alert. In other examples, ICM 10B may use Statistical Process Control that uses a variability of body stability baseline scores to see if a current body stability score is outside a normal variability.

The alert may be sent to external device 30, or a computing device 230, as examples. The alert may inform the recipient that patient 14 is having problems with body stability and the likelihood of patient 14 falling upon trying to stand is increasing. This may be indicative of deteriorating health, illness or loss of lower body and/or core strength. By sending the alert, ICM 10B may enable someone to intervene to assist patient 14.

In some examples, rather than comparing individual body stability scores 174 to the body stability baseline score 178 ICM 10B may calculate and compare a mean, median or mode body stability score to the baseline score rather than or in addition to checking each individual body stability score. In some examples, ICM 10B may discard outlier score(s) before calculating the mean, median or mode.

For simplicity purposes, the following examples are described as using a body stability mean. However, it should be understood that any central tendency measures, such as mean, median and mode may be used.

Figure 11:
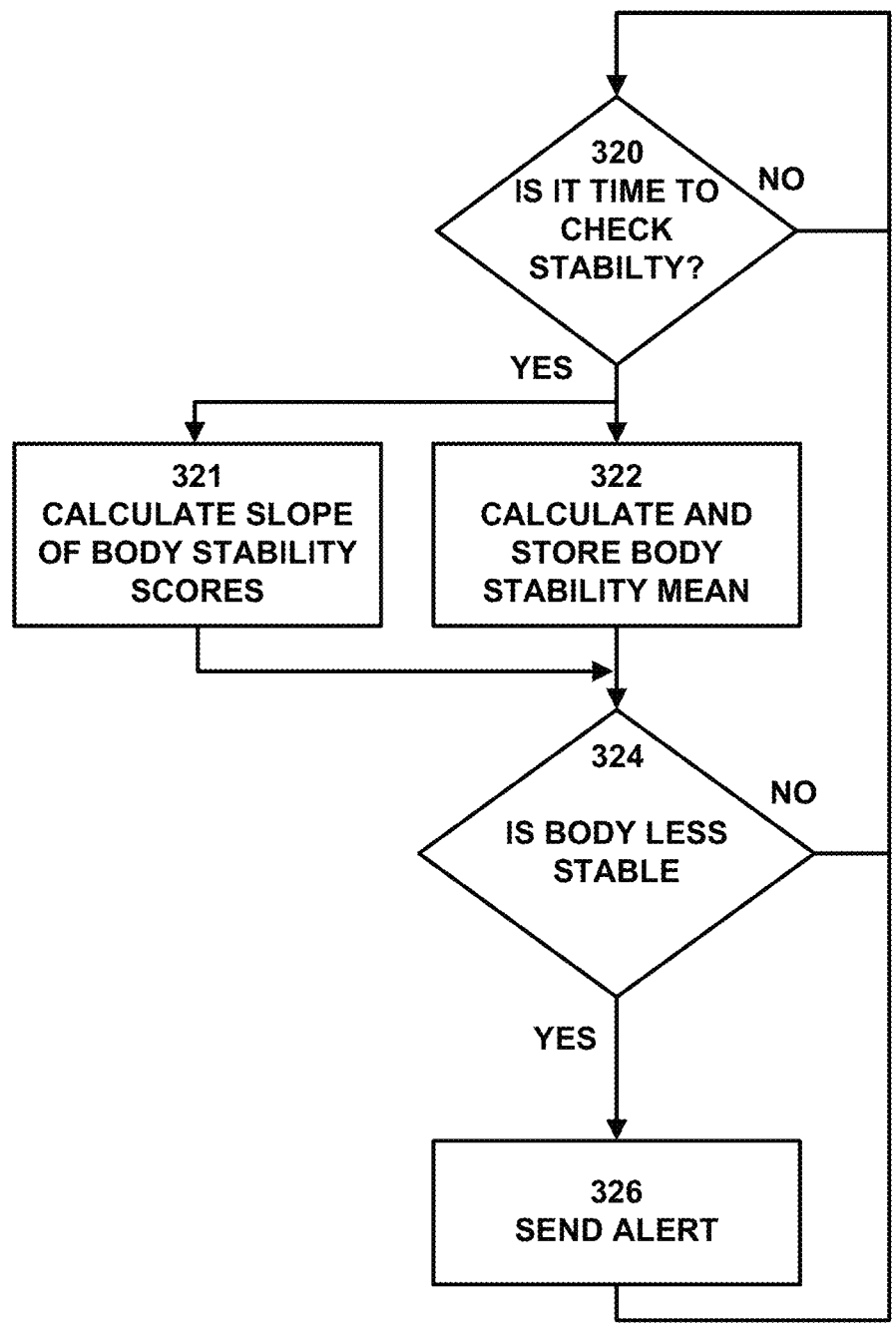
FIG. 11 is a flowchart illustrating a second example method for determining patient body stability score based on accelerometer-generated data in accordance with the disclosure.

For example, ICM 10B may periodically calculate a body stability mean 176 (for example, once a day) or may calculate a body stability mean 176 based upon a request to do so received from external device 30. FIG. 11 is a flowchart depicting an example of determining body stability based upon accelerometer data according to techniques of this disclosure. These techniques may be used in combination with the techniques of FIG. 10.

ICM 10B may check to see if it is time to check the body stability of patient 14 (320). This may be based upon a periodic time expiring (for example, one day) or receiving a request from external device 30 to check the body stability of patient 14. If it is not time to check the body stability of patient 14, ICM 10B may continue to monitor whether it is time to check the body stability of patient 14 (320). If it is time to check the body stability of patient 14, ICM 10B may calculate the mean of body stability scores 174 stored in memory 170 (322). In one example, ICM 10B calculates the body stability mean using body stability scores 174 stored within the last 24 hours. After calculating the mean, ICM 10B may store the mean in body stability mean 176 in memory 170. ICM 10B may then retain body stability scores 174, retain body stability scores 174 but flag them so they are not used to calculate body stability mean 176 again, or discard body stability scores 174.

ICM 10B may then compare body stability mean 176 to body stability baseline score 178 (324). Body stability baseline score 178 may be calculated as discussed with respect to FIG. 10. If body stability mean 176 does not deviate by a predetermined amount from body stability baseline score 178 in a way indicative of less body stability (e.g., it took longer to take the first step than the baseline score), ICM 10B may continue to monitor whether it is time to check body stability (320). In some examples, the predetermined amount may be on the order of a 50% deviation from body stability baseline score. For example, if body stability scores 174 are a measurement of the time it takes patient 14 to take the first step after a Sit-to-Stand transition and body stability baseline score is 4 seconds, if body stability mean 176 is now 6 seconds, that is on the order of a 50% deviation and may be indicative of an acute change in the body stability of patient 14.

In some examples, ICM 10B may, in addition to or in place of calculating body stability mean 176 and comparing body stability mean 176 to body stability baseline score 178, calculate a slope of individual body stability scores collected over a period of time, for example, 24 hours (321). ICM 10B may also store the slope of the individual body stability scores in memory 170. If the slope significantly deviates from zero that may be indicative of an acute change in the body stability of patient 14.

If body stability mean 176 does deviate by a predetermined amount from body stability baseline score 178 in a negative way (e.g., it took 50% longer to take the first step after transitioning) or if the slope of body stability scores 174 significantly deviate from zero, then ICM 10B may send an alert (326) to a physician, clinician, health care worker, patient 14, a family member of patient 14, a friend of patient 14 or the like. In some examples, ICM 10B may send the alert only after measuring that body stability mean 176 deviates by at least the predetermined amount from body stability baseline score 178 for two consecutive days.

In some examples, ICM 10B may monitor for chronic changes in body stability. For example, ICM 10B may determine a slope of change in body stability mean 176 over time. ICM 10B may send the alert if the slope body stability mean 176 significantly deviates from zero over a longer period of time, two weeks for example.

ICM 10B may send the alert to external device 30, for example. The alert may alert the recipient that patient 14 is having problems with body stability and the likelihood of patient 14 falling upon trying to stand is increasing. This may be indicative of deteriorating health, illness or loss of lower body and/or core strength. By sending the alert, ICM 10B may enable someone to intervene to assist patient 14.

Figure 12:
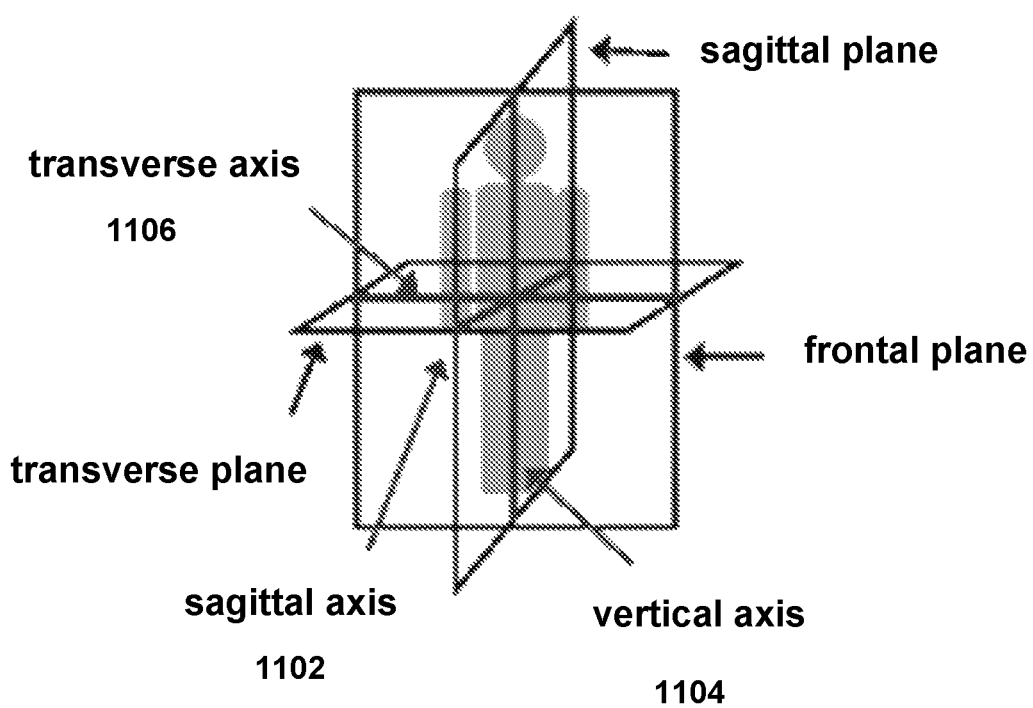
FIG. 12 is a conceptual diagram illustrating sagittal, vertical and transverse axes in a three-dimensional coordinate system.

FIG. 12 is a conceptual diagram 1100 illustrating a sagittal axis 1102, a vertical axis 1104 and transverse axis 1106 in a three-dimensional coordinate system. As can be seen, sagittal axis 1102 runs in the anterior-posterior direction, vertical axis 1104 runs vertically and transverse axis runs left-right.

Figure 13:
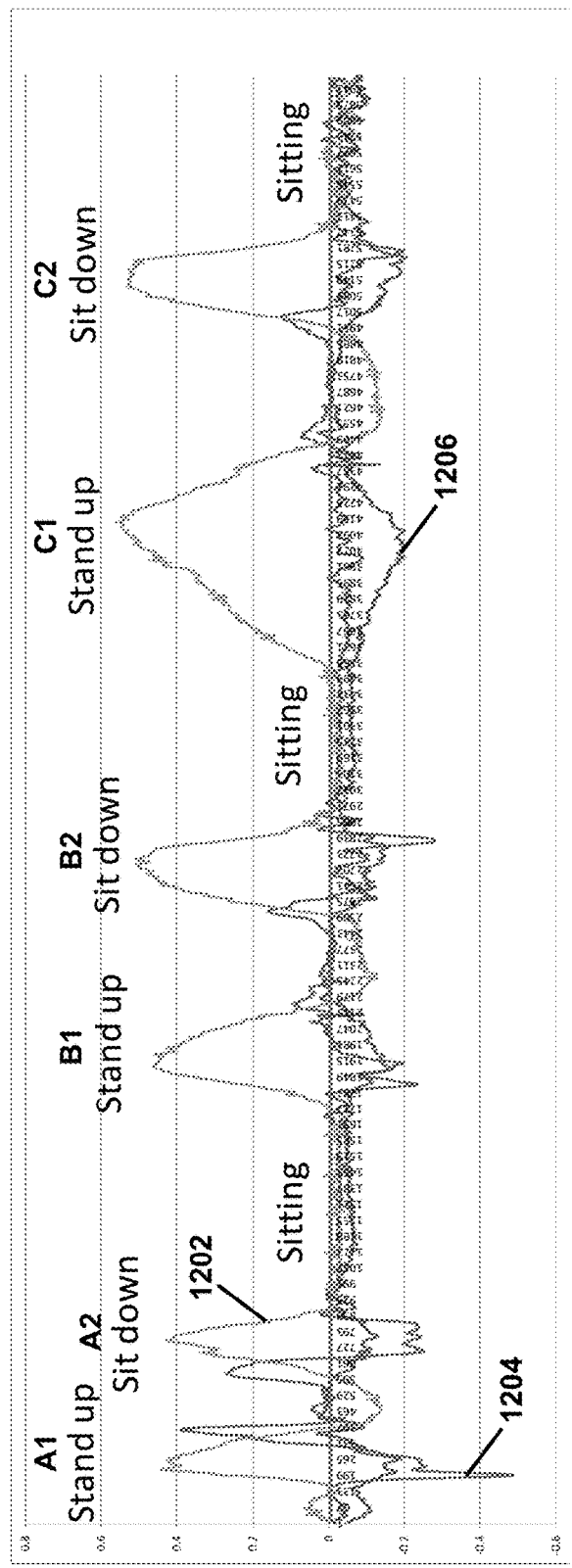
FIG. 13 is a plot illustrating sagittal, vertical and transverse axis signals produced by an accelerometer during a series of sit-stand and stand-sit movements.

FIG. 13 is a plot 1200 illustrating a sagittal axis signal 1202, a vertical axis signal 1204, and a transverse axis signal 1206 produced by an accelerometer (see e.g., FIG. 7, element 166) during a series of sit-stand and stand-sit movements labeled A1-A2, B1-B2 and C1-C2, respectively. The sagittal axis signal 1202 corresponds to the trace or trend that exhibits the largest amplitude variations primarily on the (+) side of the y-axis (arbitrary units) across each one of A1-A2, B1-B2 and C1-C2. The vertical axis signal 1204 corresponds to the trace or trend that exhibits moderate amplitude variations on the (+) side and the (−) side of the y-axis across each one of A1-A2, B1-B2 and C1-C2. The transverse axis signal 1206 corresponds to the trace or trend that exhibits amplitude variations primarily on the (−) side of the y-axis across each one of A1-A2, B1-B2 and C1-C2, exhibits a number of zero-crossings that is less than a number of zero-crossings of the vertical axis signal 1204.

The range of voltage variation provided within sagittal axis signal 1202, vertical axis signal 1204, and transverse axis signal 1206 is not limited to any particular range of voltage variation, and in some examples is the voltage variation of sagittal axis signal 1202, vertical axis signal 1204, and transverse axis signal 1206 as provided by the accelerometer configured to generated and provide the single axis accelerometer output signal processed to detect steps. In various examples, instead of sagittal axis signal 1202, a vertical axis signal 1204, and transverse axis signal 1206 showing variations in voltage relative to the vertical axis, the variations are scaled to represent variations in gravitational force, measured in units of gravity—e.g., gravity=9.80991 m/s$^2$, and the variations in sagittal axis signal 1202, vertical axis signal 1204, and transverse axis signal 1206 represent variations, measured in units, in the gravitational forces exerted in the respective axis.

Figure 14:
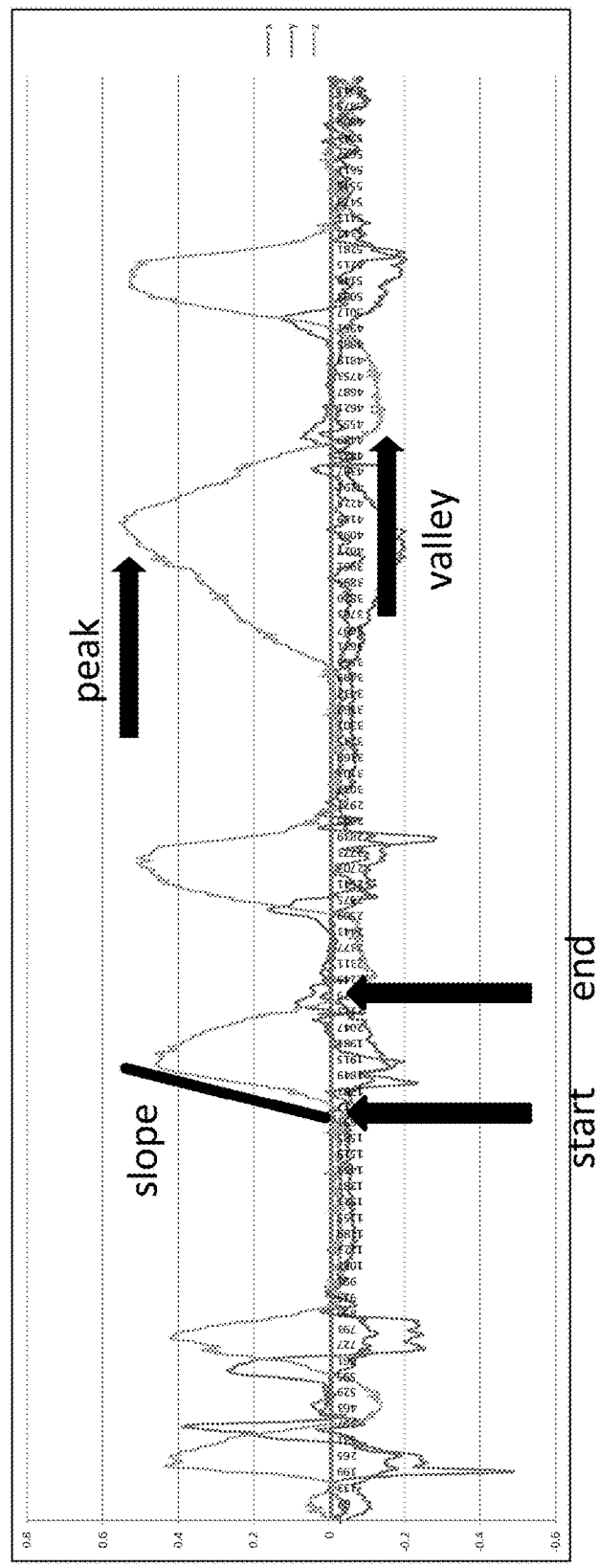
FIG. 14 is a conceptual diagram illustrating a change in several characteristics of the sagittal axis signal of FIG. 13 over the series of sit-stand and stand-sit movements.

FIG. 14 is a plot 1400 illustrating several characteristics of the sagittal axis signal of FIG. 12. The plot shows the start and end of a Sit-to-Stand transition, a peak and valley of a Sit-to-Stand transition and a slope of a Sit-to-Stand transition. As discussed above, processing circuitry 160 may determine the body stability score based on the length of time it takes from the Sit-to-Stand transition until the first step is taken by patient 14; 2) the number of peaks and/or valleys in an accelerometer signal during a predetermined period of time; 3) the amplitude of a peak to valley in an accelerometer signal during a Sit-to-Stand transition; 4) the time it takes for a peak to valley in an accelerometer signal to reach a predetermined amplitude threshold; 5) the slope of a Sit-to-Stand transition in an accelerometer signal or any combination thereof.

A medical device or system, method, and non-transitory computer-readable storage medium comprising executable instructions, for determining patient-specific body stability from accelerometer data is contemplated throughout.

For example, an implantable medical device (IMD) for determining patient-specific body stability from accelerometer data may include or comprise communication circuitry configured to establish a communication link and transfer data between the IMD intra-corpus and a computing device extra-corpus. An example of such an implementation is discussed above in connection with at least FIG. 9. The IMD may further include or comprise accelerometer circuitry configured to generate a plurality of signals including a sagittal axis signal, a vertical axis signal and a transverse axis signal. An example of such an implementation is discussed above in connection with at least FIG. 7. The IMD may further include or comprise processing circuitry configured to: calculate a patient-specific body stability score associated with a Sit-To-Stand transition from at least one of the sagittal axis signal, the vertical axis signal and the transverse axis signal; and in response to a command, activate the communication circuitry to transmit the patient-specific body stability score from the IMD to the computing device. An example of such an implementation is discussed above in connection with and shown in at least FIG. 16.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. An implantable medical device configured to be implanted in a patient comprising:
   accelerometer circuitry configured to generate at least one signal;
   communication circuitry configured to establish a communication link with an external computing device;
   a memory; and
   processing circuitry coupled to the accelerometer circuitry, the communication circuitry, and the memory configured to:
      detect a Sit-to-Stand transition of the patient in which the implantable medical device is implanted based upon the at least one signal;
      determine if the patient has been inactive for a predetermined period of time prior to the Sit-to-Stand transition based on the at least one signal;
      if the patient has been inactive for at least the predetermined period of time prior to the Sit-to-Stand transition, process the at least one signal by at least one of a) determining a first step taken by the patient after the Sit-to-Stand transition based on the at least one signal and determining a length of time from the Sit-to-Stand transition to the first step taken by the patient, b) determining a count of at least one of a number of peaks or valleys in the at least one signal during a predetermined time period associated with the Sit-to-Stand transition, c) determining an amplitude of a peak to a valley in the at least one signal, d) determining a length of time for the amplitude of the peak to the valley to reach a predetermined amplitude threshold in the at least one signal, or e) determining a slope of the at least one signal;
      determine a body stability score of the patient based on the processing of the at least one signal, the body stability score being indicative of a likelihood the patient may fall; and
      send the body stability score from the communication circuitry to the external computing device via the communication link to track health of the patient over time.

2. The device of claim 1, wherein the processing circuitry is configured to determine the body stability score based upon the length of time from the Sit-to-Stand transition to the first step taken by the patient.

3. The device of claim 1, wherein the processing circuitry is configured to determine the body stability score based upon the at least one of the number of peaks or valleys in the at least one signal during the predetermined time period associated with the Sit-to-Stand transition.

4. The device of claim 1, wherein the processing circuitry is configured to determine the body stability score based on the amplitude of the peak to valley in the at least one signal.

5. The device of claim 1, wherein the processing circuitry is configured to determine the body stability score based on the length of time for the amplitude of the peak to the valley to reach the predetermined amplitude threshold.

6. The device of claim 1, wherein the processing circuitry is further configured to monitor the patient for the Sit-to-Stand transition continuously.

7. The device of claim 1, wherein the Sit-to-Stand transition is a first Sit-to-Stand transition, the at least one signal is a first at least one signal, the predetermined period of time is a first predetermined period of time, and the body stability score is a first body stability score, and wherein the processing circuitry is further configured to:
  detect a second Sit-to-Stand transition of a patient based upon a second at least one signal;
  determine if the patient has been inactive for a second predetermined period of time prior to the second Sit-to-Stand transition; and
  if the patient has been inactive for at least the second predetermined period of time prior to the second Sit-to-Stand transition, determine a second body stability score of the patient based on the second at least one signal; and
  calculate a mean body stability score based on the first determined body stability score and the second determined body stability score.

8. The device of claim 7, wherein the processing circuitry is further configured to compare the mean body stability score to a baseline body stability score.

9. The device of claim 8, wherein the processing circuitry is further configured to:
  determine that the mean body stability score is more than a predetermined difference from the baseline body stability score; and
  send an alert from the communication circuitry to the external computing device based on the determination that the mean body stability score is more than the predetermined difference from the baseline body stability score, the alert being indicative of the patient having problems with body stability and the likelihood that the patient will fall upon trying to stand is increasing.

10. The device of claim 1, wherein the processing circuitry is configured to determine if the patient has been inactive for the predetermined period of time prior to the Sit-to-Stand transition based on the at least one signal.

11. A method comprising:
  detecting, by processing circuitry of an implantable medical device configured to be implanted in a patient, a Sit-to-Stand transition of the patient in which the implantable medical device is implanted based on at least one accelerometer signal;
  determining, by the processing circuitry, if the patient has been inactive for a predetermined period of time prior to the Sit-to-Stand transition based on the at least one signal;
  if the patient has been inactive for at least the predetermined period of time prior to the Sit-to-Stand, processing, by the processing circuitry, the at least one signal by at least one of a) determining a first step taken by the patient after the Sit-to-Stand transition based on the at least one signal and determining a length of time from the Sit-to-Stand transition to the first step taken by the patient, b) determining a count of at least one of a number of peaks or valleys in the at least one signal during a predetermined time period associated with the Sit-to-Stand transition, c) determining an amplitude of a peak to a valley in the at least one signal, d) determining a measure of time for the amplitude of the peak to the valley to reach a predetermined amplitude threshold in the at least one signal, or e) determining a slope of the at least one signal;
  determining, by the processing circuitry, a body stability score of the patient based on the processing of the at least one accelerometer signal, the body stability score being indicative of a likelihood the patient may fall; and
  sending, by communication circuitry of the implantable medical device, the body stability score to an external device via the communication link to track health of the patient over time.

12. The method of claim 11, wherein the determining the body stability score comprises determining the length of time from the Sit-to-Stand to the first step taken by the patient.

13. The method of claim 11, wherein the determining the body stability score comprises determining the at least one of the number of peaks or valleys in the at least one signal during the predetermined time period associated with the Sit-to-Stand transition.

14. The method of claim 11, wherein the determining the body stability score comprises determining the amplitude of the peak to the valley in the at least one signal.

15. The method of claim 11, wherein the determining the body stability score further comprises determining the length of time for the amplitude of the peak to the valley to reach the predetermined amplitude threshold.

16. The method of claim 11, wherein the Sit-to-Stand transition is a first Sit-to-Stand transition, the at least one signal is a first at least one signal, the predetermined period of time is a first predetermined period of time, and the body stability score is a first body stability score, and the method further comprising:
  detecting, by the processing circuitry, a second Sit-to-Stand transition of a patient based upon a second at least one signal;
  determining, by the processing circuitry, if the patient has been inactive for a second predetermined period of time prior to the second Sit-to-Stand transition; and
  if the patient has been inactive for at least the second predetermined period of time prior to the second Sit-to-Stand transition, determining, by the processing circuitry, a second body stability score of the patient based on the second at least one signal; and
  calculating, by the processing circuitry, a mean body stability score based on the first determined body stability score and the second determined body stability score.

17. The method of claim 16, further comprising comparing, by the processing circuitry, the mean body stability score to a baseline body stability score.

18. The method of claim 17, further comprising:
determining, by the processing circuitry, that the mean body stability score is more than a predetermined difference from the baseline body stability score; and
sending, by the communication circuitry, an alert to the external computing device based on the determination that the mean body stability score is more than the predetermined difference from the baseline body stability score, the alert being indicative of the patient having problems with body stability and the likelihood that the patient will fall upon trying to stand is increasing.

19. The method of claim 11, wherein determining if the patient has been inactive for the predetermined period of time prior to the Sit-to-Stand transition is based upon the at least one accelerometer signal.

20. A non-transitory computer-readable storage medium comprising instructions, that when executed by processing circuitry of an implantable medical device configured to be implanted in a patient, cause the implantable medical device to:
  detect a Sit-to-Stand transition of the patient in which the implantable medical device is implanted based upon at least one accelerometer signal;
  determine if the patient has been inactive for a predetermined period of time prior to the Sit-to-Stand transition based on the at least one signal;
  if the patient has been inactive for at least the predetermined period of time prior to the Sit-to-Stand transition, process the at least one signal by at least one of a) determining a first step taken by the patient after the Sit-to-Stand transition based on the at least one signal and determining a length of time from the Sit-to-Stand transition to the first step taken by the patient, b) determining a count of at least one of a number of peaks or valleys in the at least one signal during a predetermined time period associated with the Sit-to-Stand transition, c) determining an amplitude of a peak to a valley in the at least one signal, d) determining a length of time for the amplitude of the peak to the valley to reach a predetermined amplitude threshold in the at least one signal, or e) determining a slope of the at least one signal;
  determine a body stability score of the patient based upon the processing of the at least one accelerometer signal, the body stability score being indicative of a likelihood the patient may fall; and
  send the body stability score from communication circuitry to an external device via a communication link to track health of the patient over time.

* * * * *